US009499826B2

(12) United States Patent
Pakula et al.

(10) Patent No.: US 9,499,826 B2
(45) Date of Patent: Nov. 22, 2016

(54) PRODUCTION OF PROTEINS IN FILAMENTOUS FUNGI

(75) Inventors: Tiina Pakula, Espoo (FI); Markku Saloheimo, Espoo (FI); Mari Hakkinen, Espoo (FI); Ann Westerholm-Parvinen, Espoo (FI); Merja Penttila, Espoo (FI); Marika Vitikainen, Espoo (FI)

(73) Assignee: TEKNOLOGIAN TUTKIMUSKESKUS VTT, Espoo (FI)

( * ) Notice: Subject to any disclaimer, the term of this patent is extended or adjusted under 35 U.S.C. 154(b) by 557 days.

(21) Appl. No.: 13/701,933

(22) PCT Filed: May 30, 2011

(86) PCT No.: PCT/FI2011/050498
§ 371 (c)(1),
(2), (4) Date: Dec. 14, 2012

(87) PCT Pub. No.: WO2011/151515
PCT Pub. Date: Dec. 8, 2011

(65) Prior Publication Data
US 2013/0244276 A1    Sep. 19, 2013

(30) Foreign Application Priority Data
Jun. 4, 2010  (FI) .................................... 20105634

(51) Int. Cl.
| | |
|---|---|
| C12P 21/02 | (2006.01) |
| C12N 15/80 | (2006.01) |
| C07K 14/37 | (2006.01) |
| C12N 9/42 | (2006.01) |
| C12N 9/24 | (2006.01) |
| C12P 1/02 | (2006.01) |
| C12N 9/16 | (2006.01) |
| C12P 21/00 | (2006.01) |

(52) U.S. Cl.
CPC .............. *C12N 15/80* (2013.01); *C07K 14/37* (2013.01); *C12N 9/16* (2013.01); *C12N 9/2437* (2013.01); *C12N 9/2477* (2013.01); *C12P 1/02* (2013.01); *C12P 21/00* (2013.01); *Y02P 20/52* (2015.11)

(58) Field of Classification Search
None
See application file for complete search history.

(56) References Cited

U.S. PATENT DOCUMENTS

| | | |
|---|---|---|
| 2004/0186070 A1 | 9/2004 | Penttila et al. |
| 2011/0045526 A1* | 2/2011 | Bodie et al. ............ 435/34 |
| 2014/0004564 A1* | 1/2014 | Bodie et al. .......... 435/69.1 |

FOREIGN PATENT DOCUMENTS

| | | |
|---|---|---|
| WO | WO 2006/040312 A2 | 4/2006 |
| WO | WO 2010/034686 A1 | 4/2010 |
| WO | WO 2010/060188 A1 | 6/2010 |

OTHER PUBLICATIONS

PCT/FI2011/050498; International Search Report and Written Opinion; Nov. 14, 2011.
T. Nakari-Setala et al; Genetic Modification of Carbon Catabolite Repression in Trichoderma reesei for Improved Protein Production; Applied and Environmental Microbiology, vol. 75, No. 14, Jul. 15, 2009 (Jul. 15, 2009); pp. 4853-4860, XP055003875, ISSN: 0099-2240, DOI: 10. 1128/AEM.00282-09.
Arvas Mi Kko et al: Conmon features and interesting differences in transcriptional responses to secretion stress in the fungi Trichoderma reesei and Saccharomyces cerevisiae; BMC Genomics. Biomed Central. London. GB. vol. 7. No. 1; Feb. 22, 2006 (Feb. 22, 2006). p. 32.; XP021014630.; ISSN: 1471-2164, 001:10.1186/1471-2164-7-32.
Aro et al: Transcriptional regulation ofplant cell wall degradation by filamentous fungi; FEMS Microbiology Reviews. Elsevier. Amsterdam. NL. vol. 29. No. 4.; Sep. 1, 2005 (Sep. 1, 2005). pp. 719-739. XP005027394. ISSN: 0168-6445.
Kubicek Christian P et al: Metabolic engineering strategies for the improvement of cellulase production by Hypocrea jecorina; Biotechnology for Biofuels. Biomed Central Ltd. London UK.; vol. 2. No. 1. Sep. 1, 2009 (Sep. 1, 2009). p. 19. XP021060605. ISSN: 1754-6834. 001.
Astrid R Stricker et al: Regulation of transcription of cellulases and hemicellulases-encoding genes in Aspergillus niger and Hypocrea jecorina (Trichoderma reesei); Applied Microbiology and Biotechnology, Springer. Berlin. DE.; vol. 78. No. 2.; Jan. 16, 2008 (Jan. 16, 2008). pp. 211-220. XP019586299. ISSN: 1432-0614.
Accession No. AM 113336; Arvas, M.,, et al; Common features and interesting differences in transcriptional responses to secretion stress in the fungi Trichoderma reesei and Saccharomyces cerevisiae; BMC Genomics 7, 32 (2006).
Accession No. AMI13369; Arvas, M., et al; Common features and interesting differences in transcriptional responses to secretion stress in the fungi Trichoderma reesei and Saccharomyces cerevisiae; BMC Genomics 7, 32 (2006).
Accession No. AMI13370; Arvas, M., et al; Common features and interesting differences in transcriptional responses to secretion stress in the fungi Trichoderma reesei and Saccharomyces cerevisiae; BMC Genomics 7, 32 (2006).
Accessin No. AMI13335; Arvas, M. et al; Common features and interesting differences in transcriptional responses to secretion stress in the fungi Trichoderma reesei and Saccharomyces cerevisiae; BMC Genomics 7, 32 (2006).

* cited by examiner

*Primary Examiner* — Jim Ketter
(74) *Attorney, Agent, or Firm* — Berggren Inc.

(57) ABSTRACT

The present invention relates to a method for genetically modifying a filamentous fungus host for improved protein production. The method comprises that a filamentous fungus host is genetically modified to be deficient or to overexpress specific genes. The invention relates also to the modified hosts. Furthermore, the invention relates to a method for improved production or for producing an improved composition of proteins, such as cellulases, hemicellulases, other proteins involved in the degradation of lignocellulosic material, or other proteins, in a filamentous fungus host.

9 Claims, 33 Drawing Sheets

SEQ ID NO: 1
Strain 8-11

SEQ ID NO: 1
Strain 8-11

SEQ ID NO: 1
Strain 8-11

SEQ ID NO: 1
Strain 8-11

SEQ ID NO: 1
Strain 8-11

SEQ ID NO: 1
Strain 8-11

SEQ ID NO:2
Strain 37-18

SEQ ID NO:2
Strain 37-18

SEQ ID NO:2
Strain 37-18

SEQ ID NO:2
Strain 37-18

SEQ ID NO:2
Strain 37-18

SEQ ID NO:2
Strain 37-18

SEQ ID NO:3
Strain 13-6

SEQ ID NO:3
Strain13-6

SEQ ID NO:3
Strain 13-6

SEQ ID NO:3
Strain 13-6

SEQ ID NO:3
Strain 13-6

SEQ ID NO:3
Strain13-6

SEQ ID NO:4
Strain 26-4

SEQ ID NO:4
Strain 26-4

SEQ ID NO:4
Strain 26-4

SEQ ID NO:4
Strain 26-4

SEQ ID NO:4
Strain 26-4

SEQ ID NO:4
Strain 26-4

SEQ ID NO:5
Strain 24-1

SEQ ID NO:5
Strain 24-1

SEQ ID NO:5
Strain 24-1

SEQ ID NO:5
Strain 24-1

SEQ ID NO:5
Strain 24-1

SEQ ID NO:5
Strain 24-1

PRODUCTION OF PROTEINS IN FILAMENTOUS FUNGI

PRIORITY

This application is a national entry of PCT/FI2011/050498 filed on May 30th 2011 which claims priority of FI20105634 filed on June 4th 2010, both of which are fully incorporated herein by reference.

SEQUENCE LISTING

This application contains sequence data provided on a computer readable diskette and as a paper version. The paper version of the sequence data is identical to the data provided on the diskette.

FIELD OF THE INVENTION

The present invention relates to a method for genetically modifying a filamentous fungus host for improved protein production. The invention relates also to providing a genetically modified filamentous fungus host for improved protein production, in particular a *Trichoderma* host. Furthermore, the present invention relates to a method for improved production or for producing an improved composition of proteins in filamentous fungi. The proteins may be endogenous proteins, such as hydrolytic enzymes, or heterologous proteins.

BACKGROUND OF THE INVENTION

Many of the biopolymer degrading hydrolytic enzymes, such as cellulases, hemicellulases, ligninases and pectinases have received attention because of their potential applications in food, feed, textile, and pulp and paper industries. Industrial filamentous fungi production strains, in particular *Aspergillus* and *Trichoderma* strains, can produce high amounts of extracellular enzymes. These fungi are easy and inexpensive to grow in large bioreactors and they possess good secretion capacity capable of carrying out similar type of protein modifications as occurs in many higher eukaryotes. The existence of hypersecreting strains and strong promoters, such as cellulase promoters, make filamentous fungi hosts also potential for heterologous protein production.

It is known that the production of cellulases, hemicellulases, ligninases and pectinases are mainly regulated at the transcriptional level in filamentous fungi (Aro et al. FEMS Microbiology Reviews 29 (2005) 719-739). Stricker et al. Appl. Microbiol. Biotechnol. (2208) 78:211-220 have described the similarities and differences in the transcriptional regulation of expression of hemicellulases and cellulases in *Aspergillus niger* and *Hypocrea jecorina* (*T. reesei*), including the action of XlnR and Xyr1. In *Hypocrea jecorina* some regulatory components function in cellulase regulation positively (XYRI, ACE2, HAP2/3/5) and some negatively (ACEI, CREI) (Kubicek et al. Biotechnology and Biofuels 2009, 2:19; Nakari-Setälä et al. Appl and Environmental Microbiology, July 2009, p. 4853-4860).

Although the action of some regulatory genes on the production of cellulases and hemicellulases has been disclosed in the prior art, there is still a need for improved strains capable of enhanced or altered production of cellulases or hemicellulases or other hydrolytic enzymes in filamentous fungi.

SUMMARY OF THE INVENTION

One object of the invention is to provide a method for genetically modifying a filamentous fungus host for improved protein production.

Another object of the present invention is to provide genetically modified filamentous fungus hosts for improved protein production.

One further object of the invention is to provide a method for improved protein production or for producing improved composition of proteins in filamentous fungi.

In one aspect the invention provides a method for genetically modifying a filamentous fungus host for improved protein production. The method comprises genetically modifying a filamentous fungus host by making deficient (with reduced or lacking amount or with reduced or lacking activity) genes causing decreased production of cellulases, hemicellulases, other proteins involved in degradation of lignocellulosic material and/or other proteins;

and/or genetically modifying a filamentous fungus host to overexpress (with increased amount or activity) genes causing decreased production of cellulases, hemicellulases, other proteins involved in degradation of lignocellulosic material and/or other proteins.

In a filamentous fungus host one or more of the genes causing decreased production of cellulases, hemicellulases, other proteins involved in degradation of lignocellulosic material and/or other proteins, can be genetically modified alone or in combination.

In one aspect the invention provides a method for increasing the production of a set of proteins, typically secreted proteins, or proteins produced under the control of promoters of genes encoding secreted proteins. In another aspect the invention provides a method for reducing the production of a set of proteins, typically secreted proteins in order to modify the pattern of produced proteins or reduction of the production of unwanted side-products when producing e.g. heterologous proteins.

In various embodiments of the invention the host can be selected from the group comprising *Trichoderma, Aspergillus, Fusarium, Neurospora, Talaromyces, Phanerochaete, Chrysosporium* and *Penicillium*. In one specific embodiment the filamentous fungus host is a *Trichoderma* host.

In one embodiment of the invention a filamentous fungus host may be genetically modified to be deficient of one or more of the genes selected from the group comprising genes tre108381 (SEQ ID NO:1), tre81972 SEQ ID NO:2), tre62244 (SEQ ID NO:3), tre76677 (SEQ ID NO:4), and tre47317 (SEQ ID NO:5); or of the closest homologue of at least one of said genes in *Trichoderma, Aspergillus, Fusarium, Neurospora, Talaromyces, Phanerochaete, Chrysosporium* or *Penicillium*; or a fragment or derivative of any of said genes or other nucleotide sequence hybridizing under stringent conditions to said genes or said homologues, said host being capable of increased production of cellulases, hemicellulases, other proteins involved in degradation of lignocellulosic material and/or other proteins as compared to the production by the parental strain.

The increased production by the genetically modified strains may be detected either as higher maximal production level during the cultivation as compared to the production level of the parental strain or by higher production level at any of time points of the cultivation resulting in faster production process as compared to the parental strain.

In various embodiments of the invention filamentous fungi hosts can be constructed to be deficient for a specific gene or a combination of specific genes or by overexpressing a specific gene or a combination of specific genes, or by modifying the genes otherwise to alter the amount or activity of the protein product of the gene.

In further embodiments, filamentous fungi host strains may be constructed to be deficient for a specific gene or a combination of specific genes, and overexpressing a specific gene or a combination of specific genes, at the same time.

In one further aspect the invention provides a method for producing an improved composition of proteins in a filamentous fungus host, which comprises genetically modifying a filamentous fungus host as described above, and growing (cultivating) the modified filamentous fungus host under suitable culture conditions for protein production.

In one embodiment of the invention, the produced protein product may be an endogenous enzyme. Examples of suitable enzymes are hydrolytic enzymes, in particular cellulases, hemicellulases, cellulose or hemicelluloses side-chain cleaving enzymes, lignocellulose degrading enzymes, in particular pectinases and ligninases; amylolytic enzymes; proteases; invertases; phytases and phosphatases and hydrophobins.

In another embodiment of the invention, the protein is a heterologous or recombinant protein produced under the regulation of the promoter of a gene that is affected by the genetical modification of the host such as cellulase or hemicellulase promoter.

In one still further aspect the invention provides a genetically modified filamentous fungus host.

The host may be selected from the group comprising *Trichoderma, Aspergillus, Fusarium, Neurospora, Talaromyces, Phanerochaete, Chrysosporium* and *Penicillium*. More specifically the host may be a *Trichoderma* host.

By genetically modifying the regulatory genes or their regulatory mechanisms it is possible to improve the production of extracellular proteins in general, or the production of different sets of proteins and enzymes produced by filamentous fungi, in particular *Trichoderma*. These genetic modifications can be applied also to improve production of heterologous proteins when promoters and/or regulatory elements of genes encoding secreted proteins are used for the heterologous or recombinant expression. The fungus host can be genetically modified to express the regulatory gene more or less abundantly or to produce more or less active regulatory protein from the gene. The genetic modification can include deletion, overexpression, or any other genetic modification to alter expression strength of the gene or the activity of the product of the gene. The genetical modifications result in a desired effect on the produced protein pattern by the fungal production host. It may be beneficial to genetifically modify the production hosts in such a way that production of unwanted side products is reduced, or in such a way that a selected protein or a set of proteins are more abundantly expressed and other proteins produced less abundantly. Corresponding genetic modifications can be done also in other filamentous fungi, in order to modify protein production properties of the host, by modifying the corresponding homologous genes. In addition the corresponding genes from other fungal species can be introduced, as such or in a modified form, to other fungal species to get the desired effect on protein production in the other organism.

In the following text, the invention will be further described with the aid of a detailed description and with reference to some working examples.

DETAILED DESCRIPTION OF THE INVENTION

Figure 1:
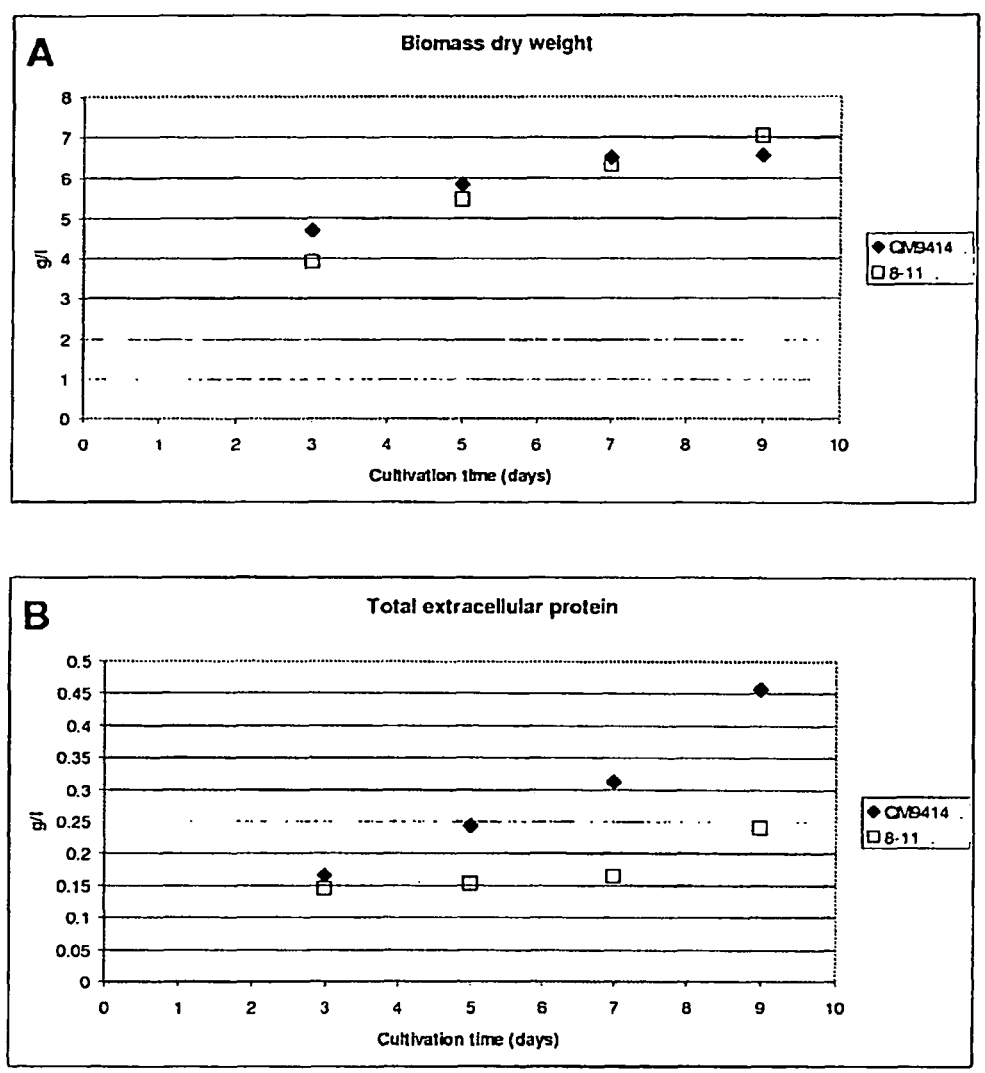
FIG. 1-5 present the results of protein production by strains genetically modified to overexpress a specific gene.
Figure 1:
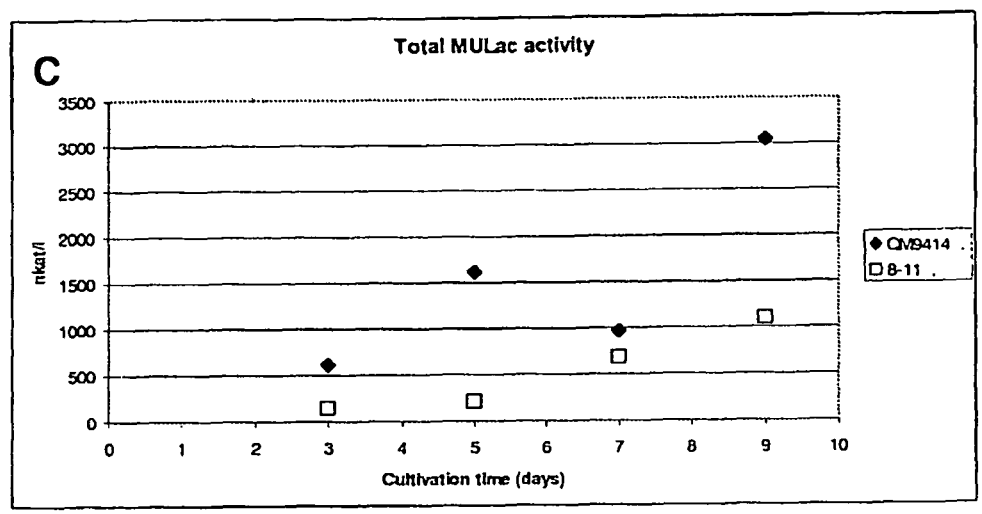
Figure 1:
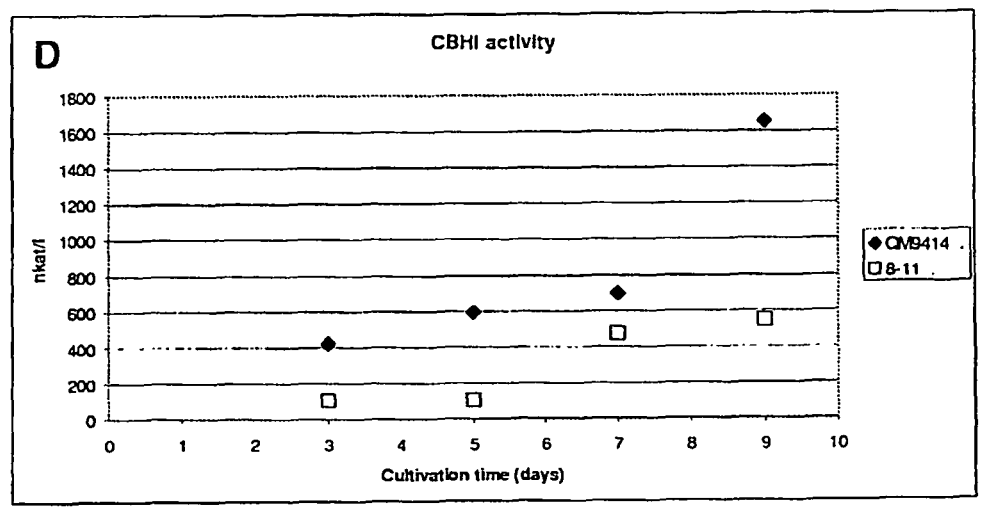
Figure 1:
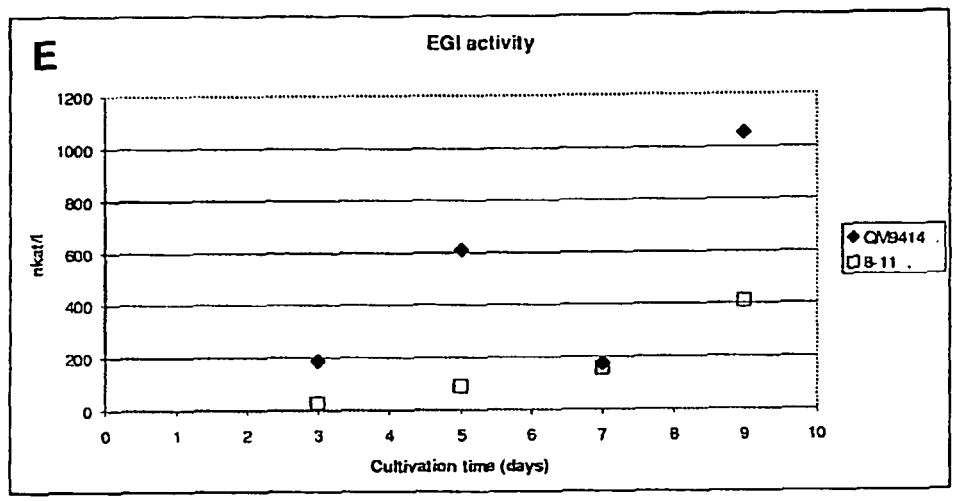
Figure 1:
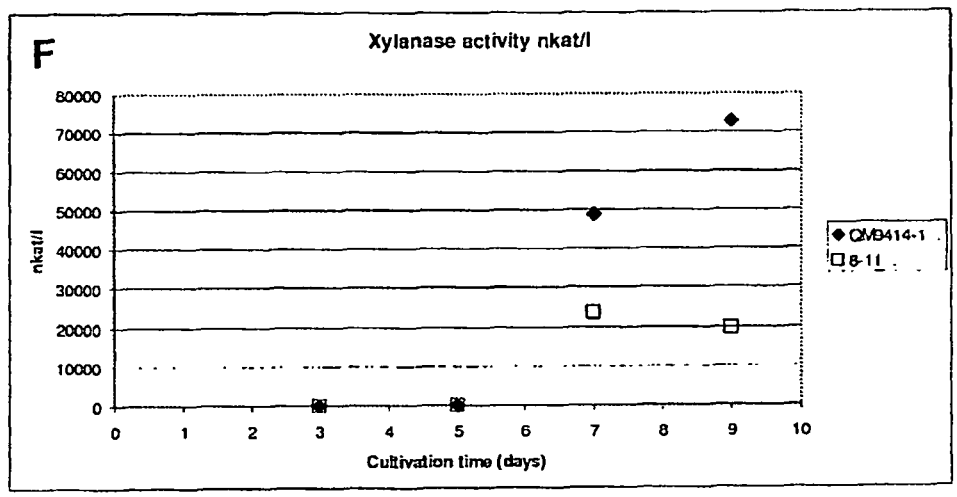
Figure 1:
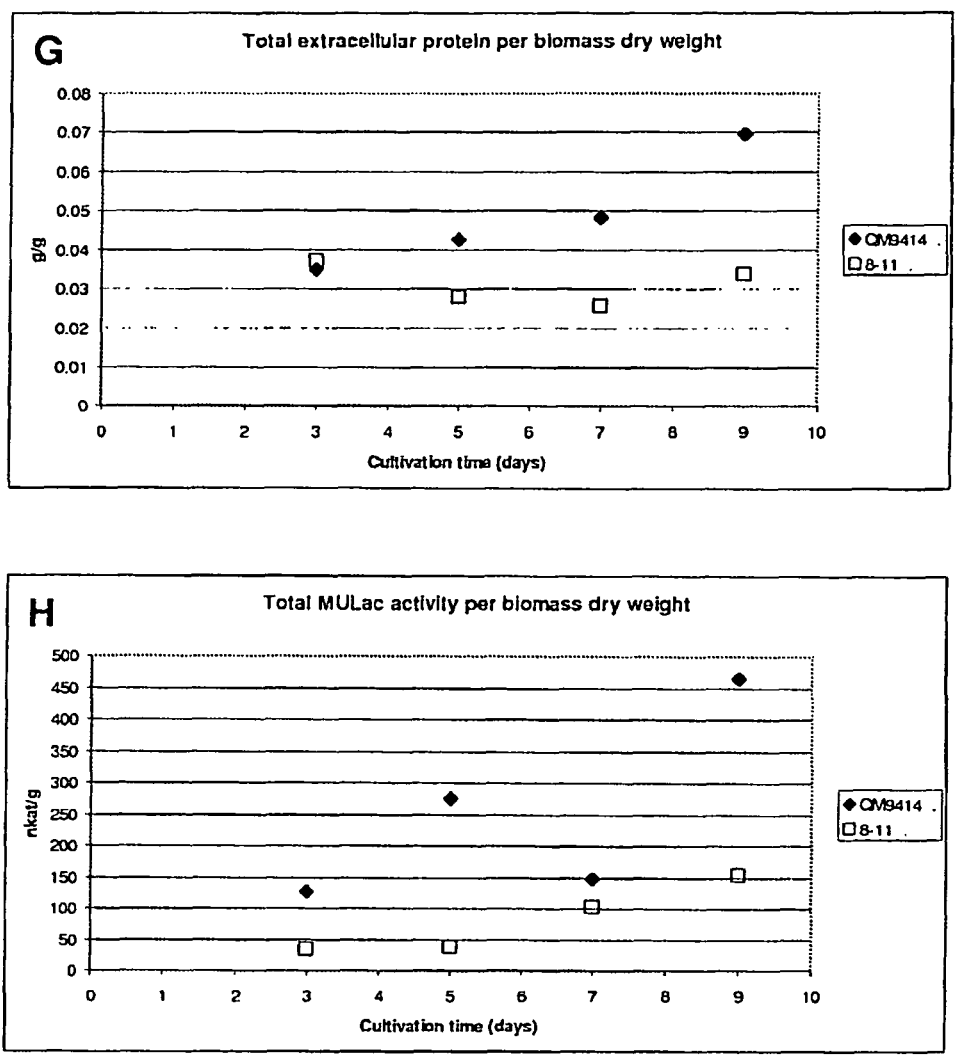
Figure 1:
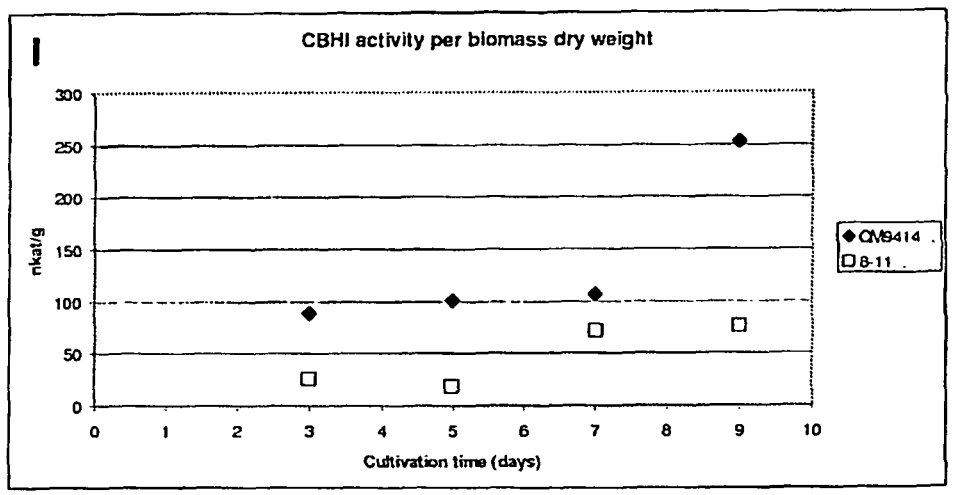
Figure 1:
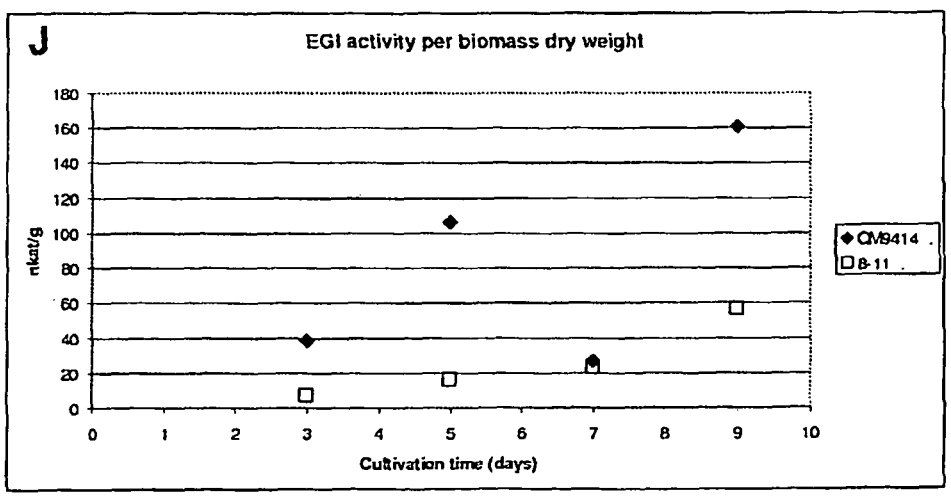
Figure 1:
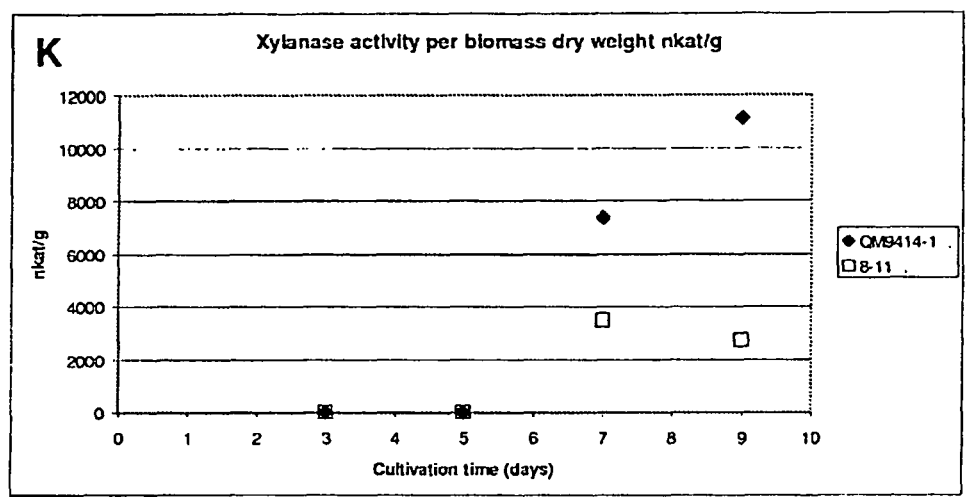

The present invention relates to improved production of various proteins in filamentous fungi. The invention is based on the finding of regulatory factors which affect the production of various proteins, in particular hydrolytic enzymes. Within the scope of the present invention are cellulases, such as cellobiohydrolases, endoglucanases and β-glucosidases; and hemicellulases, such as xylanases, mannases, β-xylosidases; and side chain cleaving enzymes, such as arabinosidases, glucuronidases, acetyl xylan esterases; and other lignocellulose degrading enzymes, in particular pectinases, such as endo- and exopolygalacturonases, pectin esterases, pectin and pectin acid lyase; and ligninases, such as lignin peroxidases, Mn peroxidases, laccases; amylolytic enzymes, such as α-amylases, glucoamylases, pullulanases, cyclodextrinases; hydrophobins; proteases (serine, aspartic, glutamic, metallo proteases, acidic, alkaline); invertases; phytases; and phosphatases, and hydrophobins.

By overexpressing specific genes and/or by making deficient specific genes which encode the regulatory factors in the fungal host, it is possible to increase or alter the production of endogenous proteins, in particular hydrolytic enzymes, such as cellulases, hemicellulases, lignocellulose degrading enzymes, other proteins involved in the degradation of lignocellulosic material, or other proteins, typically secreted proteins. It is also possible to produce heterologous or recombinant proteins under the regulation of the promoters of the affected genes, such as cellulase or hemicellulase gene promoter, or promoters of other genes encoding proteins involved in the degradation of lignocellulosic material or other secreted protein promoters, by good yield in the modified host.

Described herein are methods used in modifying filamentous fungi hosts, such as *Trichoderma, Aspergillus, Fusarium, Neurospora, Talaromyces, Phanerochaete, Chrysosporium* and *Penicillium*. In these methods are used genes selected based on expression of the genes in cultures grown on different substrates and by sequence data of the genes. The sequence preferably comprises a sequence domain characteristic for genes encoding regulatory proteins, such as transcription factors, other transcriptional regulators, protein kinases, proteins involved in histone modification or chromatin remodelling, or the genes are preferably co-regulated with cellulase or hemicellulase genes in the genome of a filamentous fungus host.

"Making deficient of a gene" means either a genetic modification of the fungus host to delete or truncate a specific gene (here in particular a regulating gene) or a genetic modification of the fungus host resulting in reduced or lacking expression of the gene or reduced or lacking activity of the gene product by any suitable method. By "inactivation" is meant a genetic modification (usually deletion) resulting in complete loss of activity of a gene product.) In this invention, the effect of the genetic modification of a specific gene on protein production can be studied by determining for example a specific enzyme activity, determining the amount of total protein, or determining the amount of specific endogenous or heterologous protein produced.

"Overexpression of a gene" (here in particular a regulating gene) can be carried out for example by introducing into a fungus host an additional copy or copies of a specific gene, or expressing the gene under another promoter resulting in increased expression of the gene, or otherwise genetically modifying the fungus host so that either the gene is more abundantly expressed or the the activity of the gene product is increased. The effect of overexpression of a gene on protein production can be studied by culturing the modified host under conditions suitable for protein production. The effect on the production of an endogenous protein or proteins can be studied by determining for example a specific enzyme activity, determining the amount of total protein, or determining the amount of specific endogenous or heterologous protein produced.

By "a regulatory gene" is meant here a gene whose function has an effect on production of proteins by the fungal host. "Overexpression of the gene" (as described above) or "making deficient of a gene" (as described above) has an effect on protein production by the fungus. The gene can encode for example a transcription factor, other transcriptional regulator, a protein kinase, a protein involved in histone modification or chromatin remodelling, or other regulatory protein.

By "inducing substrates" are meant here substrates capable of inducing the production of hydrolytic enzymes or lignocelluloses degrading enzymes, such as cellulase or hemicellulase, other protein involved in the degradation of lignocellulosic material, or other proteins, typically secreted proteins or proteins produced using promoters of genes encoding secreted proteins. For the purpose of studying the genes encoding the mentioned enzymes, for example substrates, such as Avicel®, pretreated wheat straw, pretreated spruce, lactose, spent grain extract or sophorose, or other plant derived carbon sources, can be used. Pretreatment of spruce and wheat can be carried out by using steam explosion and washing the treated material. The fibrous fraction of the material can be used for the induction.

By "suitable culture conditions for protein production" is meant here any culture conditions suitable for producing a desired protein or a combination of desired proteins. Conditions for producing hydrolytic enzymes or lignocelluloses degrading enzymes, such as cellulase or hemicellulase, other protein involved in the degradation of lignocellulosic material or for many secreted or other proteins, are well known for a person skilled in the art.

In one aspect improved production may mean improved production of a desired enzyme or other protein. As disclosed herein a filamentous fungus host may be constructed to be deficient in a specific regulatory gene or genes, or may be constructed to overexpress a specific other regulatory gene or genes in order to improve the protein production.

By "improved production" is here meant in one aspect increased amount of protein produced. The protein may be produced into the culture medium or into the host cell, preferably into the culture medium. Increased production may be detected for example as higher maximal level of protein or enzymatic activity, such as cellulase or hemicellulase activity, or total extracellular protein produced as compared to the parent host. In addition, or alternatively, improved protein production may be detected as a higher level of produced enzymatic activity or protein produced at any time point of cultivation which results in higher production level at earlier stages in cultivation and thus in faster production process as compared to parent host strain. Improved production may mean also increased production of secreted protein or enzymatic activity per biomass amount in the culture. Protein production by a lower amount of biomass is beneficial due to easier down stream-processing of the protein product and reduced consumption of nutrients during the production process. Also, a desired effect of the genetic manipulation of the production strain is lowered viscosity of the production culture due to e.g. lowered biomass amount in the production process or due to other properties of the strain. Cellulase and hemicellulase activities can be measured using a variety of methods using different substrates (for examples of the methods, see: Zhang Y. H., Hong J., Ye X., Cellulase assays, Methods Mol. Biol., (2009), 581:213-231; Sharrock K. R., Cellulase assay methods: a review, J. Biochem. Biophys. Methods. (1988),17: 81-105; T. K. Ghose, Measurement of cellulase activities, (1987), Pure & Appl. Chem., 59, 257-268; T. K. Ghose and V. S. Bisaria, Measurement of hemicellulase activities. Pure & Appl. Chem., (1987), 59, 1739-1752). Cellulase activity can be measured e.g. as enzymatic activity against the substrate, 4-methylumbelliferyl-β-D-lactoside (MULac). Methods for measuring the combined activity of CBHI, EGI and β-glucosidase (referred here as "total MULac" activity), as well as the separate activities of the enzymes, using MULac as substrate have been described (Bailey and Tähtiharju, 2003; Collen et al., 2005; van Tilbeurgh et al., 1982, 1985, 1988). Other substrates often used for cellulase activity measurements include e.g. CMC cellulose, hydroxyethylcellulose and filter paper. The hemicellulase activity can be measured e.g. as activity against the birch xylan substrate (Bailey et al., 1992, Bailey M. J., Biely, P. and Poutanen, K. (1992) Interlaboratory testing of methods for assay of xylanase activity. J. Biotechnol. 23: 257-270), and production of total extracellular protein by using any of the methods for measurement of protein concentration known in the art, for example using Bio-Rad Protein Assay (Bio.Rad) Growth and progress of the cultivation of filamentous fungi can be determined by measuring the production of biomass and by measuring the pH of the culture medium. Induction of protein production, and differences in gene expression level can be analysed by isolation of RNA and subjecting the samples to micro array hybridisation analysis or Northern hybridisation or TRAC analysis (Rautio, J. J., Smit, B. A., Wiebe, M., Pennila, M. & Saloheimo, M. 2006. Transcriptional monitoring of steady state and effects of anaerobic phases in chemostat cultures of the filamentous fungus *Trichoderma reesei*. BMC Genomics 7, article number 247. 15 p. 10.1186/1471-2164-7-247)

Improved CBHI activity may be detected by higher production level of enzyme activity against MULac substrate using a method modified for analysis of CBHI activity.

Improved EGI activity may be detected by higher production level of enzyme activity against MULac substrate and especially by higher activity against MULac substrate under conditions measuring specifically the activity of EGI.

The increased hemicellulase production may be detected by higher production level of enzyme activity against birch xylan substrate.

In one embodiment the protein can be an endogenous protein, in particular a hydrolytic enzyme, such as cellulase, hemicellulase or lignocellulose degrading enzyme, or other secreted protein. More specifically the protein can be a cellulase or hemicellulase.

In another embodiment the protein may be any protein which is produced under the promoter of the affected endogenous genes. The protein may be produced for example under various cellulase or hemicellulase gene promoters, such as promoters or genes encoding CBHI, EGI or XYNI.

Improved protein production may mean altered content of the proteins produced by the fungus host, and production of a desired protein or a protein mixture. As disclosed herein a filamentous fungus host may be constructed to be deficient in a specific regulatory gene or genes, or may be constructed to overexpress a specific other regulatory gene or genes in order to alter the protein production compared to the parental host.

By the term "endogenous proteins" are meant here proteins which are natural products of a filamentous fungus host.

By "a heterologous protein" is meant a protein that is not a natural product of the fungal species.

By "recombinant proteins" are meant here proteins that are not natural products of a filamentous fungus or that are produced by a non-natural construction in a filamentous fungus. DNA sequences encoding desired homologous or heterologous proteins may be transferred by a suitable method to a host.

By "secretable protein" or "secreted protein" is meant here a protein that is secretable or secreted outside of the host cell to the culture medium.

By reduced protein production is meant protein production which is at least 3%, preferably at least 5%, more preferably at least 10%, still more preferably at least 20%, still more preferably at least 30% or most preferably at least 50% lower than protein production by using the parent fungal host strain which has not been genetically modified. By increased protein production is meant protein production which is a least 3%, preferably at least 5%, more preferably at least 10%, still more preferably at least 20%, still more preferably at least 30% or most preferably at least 50% better than protein production by using the parent fungal host strain which has not been genetically modified.

One embodiment of the invention comprises the expression of gene sequences responsive of regulating the production of hydrolytic enzymes. The genes may increase or decrease the enzyme production, or they may increase the production of some enzyme activities and decrease other enzyme activities.

"Genetical modification" of a filamentous fungus host means here any genetic modification method by which a filamentous fungus host is modified to overexpress a specific regulatory gene or to gain modified properties of the gene or genes and/or to be deficient of the gene or genes, Genetical modification methods for the strains of *Trichoderma*, *Aspergillus*, *Fusarium*, *Neurospora*, *Phanerochaete*, *Talaromyces*, *Chrysosporium* and *Penicillium* are available and well known for a person skilled in the art (Sambrook et al., 1989, Pennila et al., 1987; Jain et al., 1992; Austin et al., 1990; Bull et al., 1988; Maier et al., 2005; Akileswaran et al., 1993).

Pennila M, Nevalainen H, Rättö M, Salminen E, Knowles J. (1987) A versatile transformation system for the cellulolytic filamentous fungus *Trichoderma reesei*. Gene. 1987; 61:155-64.

Jain S, Durand H, Tiraby G. (1992) Development of a transformation system for the thermophilic fungus *Talaromyces* sp. CL240 based on the use of phleomycin resistance as a dominant selectable marker. Mol Gen Genet. 1992 September; 234(3):489-93.

Austin B, Hall R M, Tyler B M. (1990) Optimized vectors and selection for transformation of *Neurospora crassa* and *Aspergillus nidulans* to bleomycin and phleomycin resistance. Gene. 1990 93:157-62.

Bull J H, Smith D J, Turner G. (1988) Transformation of *Penicillium chrysogenum* with a dominant selectable marker. Curr Genet. 1988 May; 13(5):377-82.

Maier F J, Malz S, Lösch A P, Lacour T, Schäfer W. (2005) Development of a highly efficient gene targeting system for *Fusarium graminearum* using the disruption of a polyketide synthase gene as a visible marker. FEMS Yeast Res. 2005 April; 5(6-7):653-62.

Akileswaran L, Alic M, Clark E K, Hornick J L, Gold M H. (1993) Isolation and transformation of uracil auxotrophs of the lignin-degrading basidiomycete *Phanerochaete chrysosporium*. Curr Genet. 1993; 23(4):351-6.

By "gene" is meant here in particular a gene or genes encoding regulatory proteins, such as transcription factors, other transcriptional regulators, protein kinases, proteins involved in histone modification or chromatin remodelling, or genes located near cellulase or hemicellulase genes (co-expressed) in the genome of a filamentous fungus host. The genes have been selected by using the method as described herein. The function of the genes has been exemplified in *Trichoderma*, in particular in *T. reesei* which show the effect of these genes in protein production. Modification of the genes in other filamentous fungi, in particular *Aspergillus* will be useful for improved protein production. The "gene" in the present invention is preferably a *Trichoderma* gene. Within the scope of the present invention are also the closest homologues of the genes in other species of filamentous fungi and nucleotide sequences hybridizing under stringent conditions to said genes or said homologues. Within the scope of the present invention are also fragments, derivatives or other nucleotide sequences of said genes hybridizing under stringent conditions to said genes or said homologues. The "gene" may be isolated, which means that it is isolated from its natural components. The "gene" may be partly or completely synthetic. Within the scope of the present invention are also derivatives of said gene, which refers to nucleic acid sequences comprising deletions, substitutions, insertions or other modifications compared to said gene, but having the same or equivalent function as said gene.

A "fungal host" denotes here any fungal host strains selected or genetically modified to produce or not to produce efficiently a desired product and is useful for protein production for e.g. analytical, medical or industrial use. A fungal host is in particular "a fungal production host" that is suitable for industrial production of certain protein products. The host strain is preferably a recombinant strain modified by gene technological means to efficiently produce a product of interest. The fungal host may belong for example to *Trichoderma, Aspergillus, Fusarium, Neurospora, Talaromyces,* Phanerochaete, *Chrysosporium* or *Penicillium* genera. Typically the host is *Trichoderma* or *Aspergillus* host.

The "closest homologue of a *Trichoderma* gene" in other species of filamentous fungi means here a gene that has the highest percentage of identical nucleotides with the *Trichoderma* gene of all the genes of the organism; or a gene whose protein product has the highest percentage of identical amino acids with the protein product encoded by the *Trichoderma* gene of all the gene products of the organism. The sequence identity of homologous regulatory genes in different organisms is typically very low. Typically, the sites binding either to DNA or other protein factors involved in the regulation event share homology, but the intervening sequences between these sites may not be conserved. Therefore the total % of sequence identity of homologous regulatory genes in different organisms remains relatively low. However, the percentage of sequence identity in the aligned nucleotide sequence can be used as a measure to identify the closest homologue of the gene in the other organism; thus a likely functional counterpart of the gene in the other organism. Software and algorithms for homology searches as well as public databases with whole genome sequence information for a variety of species exist, such as the BLAST program (Stephen F. Altschul, Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402. Reference for compositional score matrix adjustment: Stephen F. Altschul, John C. Wootton, E. Michael Gertz, Richa Agarwala, Aleksandr Morgulis, Alejandro A. Schaffer, and Yi-Kuo Yu (2005) "Protein database searches using compositionally adjusted substitution matrices", FEBS J. 272:5101-5109) and the NCBI database.

A specific "gene" is here represented by a specific sequence (SEQ ID NO)". The effect of the gene has been shown by using the sequence of a specific SEQ ID NO (which is here a *Trichoderma* sequence). The sequence may comprise additional sequence in front of and/or after the coding region of the gene. As described here, instead of the *Trichoderma* sequence, the closest homologue from another filamentous fungus could be used. As is known to a person skilled in the art, also sequences hybridizing under stringent conditions to the *Trichoderma* sequence or to its closest homologue, could be used, wherein stringent conditions refer here to an overnight incubation at 42 degree C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65 degree C.

The detection methods of cellulase activity, CBI-II activity or EGI activity are well known for a person skilled in the art. The methods are described for example in Bailey and Tähtiharju, 2003; Collen et al., 2005; van Tilbeurgh et al., 1982, 1985, 1988. Collén, A., Saloheimo, M., Bailey, M., Penttilä, M. & Pakula, T. M. (2005) Protein production and induction of the unfolded protein response in *Trichoderma reesei* strain Rut-C30 and its transformant expressing endoglucanase I with a hydrophobic tag. *Biotech. Bioeng.* 89, 335-344. Bailey M J, Tahtiharju J. 2003. Efficient cellulase production by *Trichoderma reesei* in continuous cultivation on lactose medium with a computer-controlled feeding strategy. Appl Microbiol Biotechnol 62:156-62.van Tilbeurgh H, Claeyssens M, de Bruyne C. 1982. The use of 4-methylumbelliferyl and other chromophoric glycosidases in the study of cellulolytic enzymes. FEBS Lett 149:152-156.van Tilbeurgh H, Loontiens F G, de Bruyne C K, Claeyssens M. 1988. Fluorogenic and chromogenic glycosides as substrates and ligands of carbohydrates. Methods Enzymol 160:45-59.van Tilbeurgh H, Pettersson G, Bhikabhai R, De Boeck H, Claeyssens M. 1985. Studies of the cellulolytic system of *Trichoderma reesei* QM 9414. Reaction specificity and thermodynamics of interactions of small substrates and ligands with the 1,4-beta-glucan cellobiohydrolase II. Eur J Biochem 148:329-34.

The cultures of the strains modified for the regulatory genes can be analysed for the produced protein pattern more in detail using a broader set of enzyme activity measurements specific for different enzymes. In addition, the produced protein pattern can be analysed using 2D gel electrophoresis followed by identification of the proteins by mass spectrometry. The 2D gel analysis can reveal also quantitative differences in the produced protein patterns between the cultures of the different strains. This information can reveal specific sets of produced proteins that are affected by the specific genetic modification. Furthermore, additional genetically modified strains can be constructed to be able to analyse the effects of both the overexpression and the deficiency (typically deletion) of the gene, and by these means to reveal the target genes and proteins whose function is affected by the modification of the gene, and to demonstrate the effect of the specific gene modification on the produced protein pattern. These genetically modified strains can also be subjected to transcriptional profiling in order to elucidate the effect of the genetic modification on the gene expression levels and to reveal target genes affected by the modification. The information of the effects of the genetic modification on the produced protein pattern (from the enzyme assays and 2D gel analysis of the culture supernatants) as well as information on the transcriptional responses caused by the genetic modification, and the target genes for the regulatory events it is possible to modify the protein production properties and efficiency, as well as the composition of the protein mixture produced into the culture medium in a defined way.

The improvement in protein production process can mean either increased production of all the secreted proteins, or improved production of a specific set of proteins, or reduced production of unwanted products, or a faster or shorter production process for the protein, or a production process with less consumption of nutrients for other products than proteins (e.g. for biomass, or unwanted side-products), or better physico-chemical properties protein producing unit (e.g. less viscose cultivation, better morphology of the production host), or better down-stream processing properties of cultivation and the protein product, or better physico-chemical quality of the product.

Increased production of extracellular proteins or different enzyme activities can be obtained by making the fungal host deficient of genes that are harmful to production of the said proteins or enzymes. To increase the production of cellulase or hemicellulase activities, or other proteins, typically secreted proteins, or proteins produced using promoters of genes encoding secreted proteins, such genes to be made deficient in the production host include one more of the genes tre108381 (SEQ ID NO:1), tre81972 SEQ ID NO:2), tre62244 (SEQ ID NO:3), tre76677 (SEQ ID NO:4), and tre47317 (SEQ ID NO:5) Table 1); or the closest homologue of at least one of said genes in *Trichoderma, Aspergillus, Fusarium, Neurospora, Talaromyces*, Phanerochaete, *Chrysosporium* or *Penicillium*; or a fragment or derivative of any of said genes or other sequence hybridizing under stringent conditions to at least one of said sequences or said homologues. These genes cause decreased production of cellulase, hemicellulase activity and/or total amount of protein when overexpressed in the production host.

Cellulase acitivity can be measured e.g. as enzymatic activity against the substrate, 4-methylumbelliferyl-β-D-lactoside (MULac). Methods for measuring the combined activity of CBHI, EGI and β-glucosidase (referred here as "total MULac" activity), as well as the separate activities of the enzymes, using MULac as substrate have been described by Bailey and Tahtiharju, 2003; Collen et al., 2005; van Tilbeurgh et al., 1982, 1985, 1988. The hemicellulase activity can be measured e.g. as activity against the birch xylan substrate (Bailey et al., 1992, Bailey M. J., Biely, P. and Poutanen, K. (1992) Interlaboratory testing of methods for assay of xylanase activity. J. Biotechnol. 23: 257-270), and production of total extracellular protein by using any of the methods for measurement of protein concentration known in the art, for example using Bio-Rad Protein Assay (Bio.Rad)

It is advantageous, if one or more of genes tre108381 (SEQ ID NO:1), tre81972 SEQ ID NO:2), tre62244 (SEQ ID NO:3), still more preferably either one or both of genes tre108381 (SEQ ID NO:1) and/or tre81972 SEQ ID NO:2), are made deficient in a fungus host. The term "gene" encompasses here also the closest homologue of at least one of said sequences in *Aspergillus, Fusarium, Neurospora, Talaromyces, Phanerochaete, Chrysosporium* or *Penicillium*; or a fragment or derivative of said genes or other nucleotide sequence hybridizing under stringent conditions to at least one of said sequences or said homologues.

erties of the fungus host. Overexpression of one or more of the genes can be used to decrease production of the cellulase and hemicellulase activities or other proteins, typically secreted proteins or proteins produced using promoters of genes encoding secreted proteins. Thus, overexpression of one or more of the genes can be used to reduce the amount of unwanted side-products to be produced or to modify the protein pattern produced. Within the scope of protection are thus genetical modification of a fungus host by making deficient or overexpressing at least one of said genes. Overexpression of the above mentioned genes in filamentous fungus hosts was exemplified here by constructing *Trichoderma* strains expressing these genes.

The expression of the same or corresponding genes i.e. closest homologues of said genes, in other filamentous fungi hosts, is within the scope of protection of the present invention.

Also sequences hybridizing under stringent conditions to the *Trichoderma* genes or their closest homologues in other filamentous fungus hosts are within the scope of protection of the present invention. In the following text, by "gene" is meant also the closest homologue of the gene or sequences hybridizing into said gene or said homologue as herein described. By "gene" is in the following text meant also any derivative or modified form comprising deletions, substitutions, insertions or other genetic modifications, but having the same or equivalentic function as the said "gene".

To exemplify the effect of the genes on protein production, the genes were overexpressed in *T. reesei* QM9414 host as described in the Examples 4-6.

The structure of the genes is similar in that they all comprise a sequence domain typical to genes encoding regulatory proteins, such as transcription factors as shown in Table 2.

TABLE 2

| Gene ID | | IPR001138, Fungal transcriptional regulatory protein, N-terminal | IPR007219, Fungal specific transcription factor | IPR001251, Cellular retinaldehyde-binding/triple function, C-terminal | IPR008273, Cellular retinaldehyde-binding/triple function, C-terminal |
|---|---|---|---|---|---|
| tre108381 | pMH 8 | x | | | |
| tre81972 | pMH37 | | | x | x |
| tre62244 | pMH 13 | x | x | | |
| tre76677 | pMH 26 | x | x | | |
| tre47317 | pMH 24 | | x | | |

TABLE 1

| Plasmid | T. reesei gene | strain |
|---|---|---|
| pMH24 | tre47317 | 24-1 |
| pMH13 | tre62244 | 13-6 |
| pMH26 | tre76677 | 26-4 |
| pMH8 | tre108381 | 8-11 |
| pMH37 | tre81972 | 37-18 |

The corresponding genes may also be made deficient as described above, also in other filamentous fungi hosts.

Also other combinations of the mentioned genes can be made dificient and/or overexpressed in a fungus hosts to get a combined effect of the genes on protein production prop- The effect of gene tre108381 (FIG. 1), represented by SEQ ID NO:1, was exemplified by constructing strain *T. reesei* 8-11 overexpressing the gene. The overexpression of the gene had a negative effect on protein production. The overexpression strain 8-11 produced less total extracellular protein, less cellulase activity (measured as total MULac, GBH or EGI activity) or hemicellulase activity (measured as activity on xylan substrate) as compared to the cultures of the parental starin. Inactivation of the gene 108381 is expected to remove the negative effect on protein production, and inactivation of the gene is expected to result in improved production of cellulases, hemicellulases, other secreted proteins, or heterologous proteins produced under cellulase or hemicellulase gene promoters.

Figure 2:
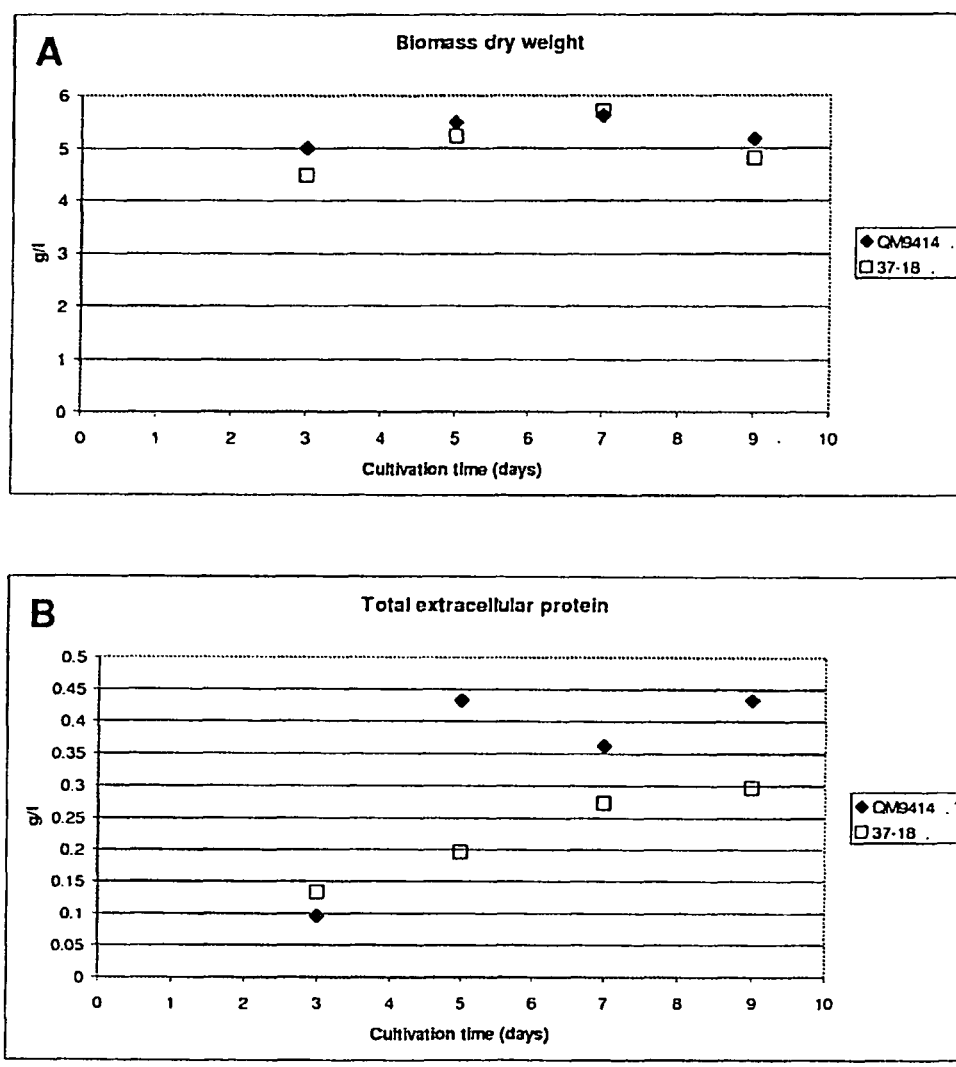
Figure 2:
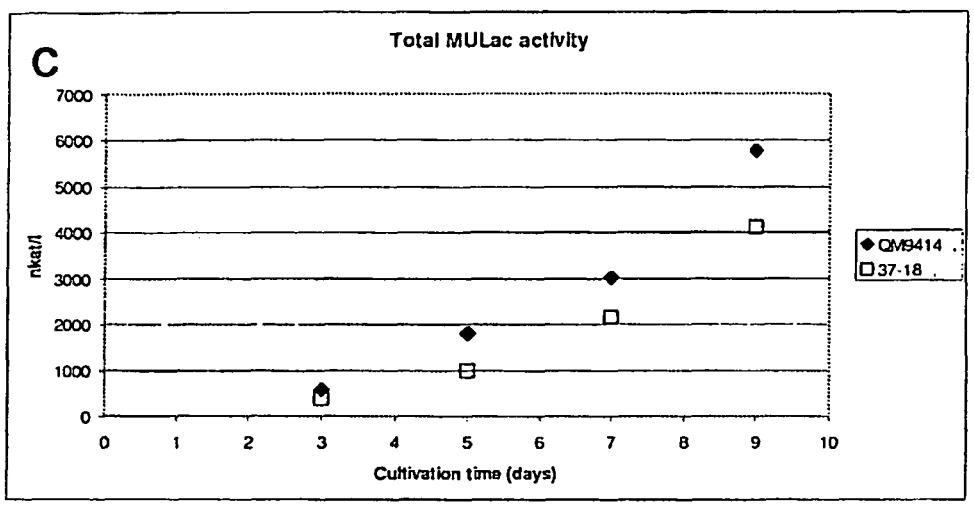
Figure 2:
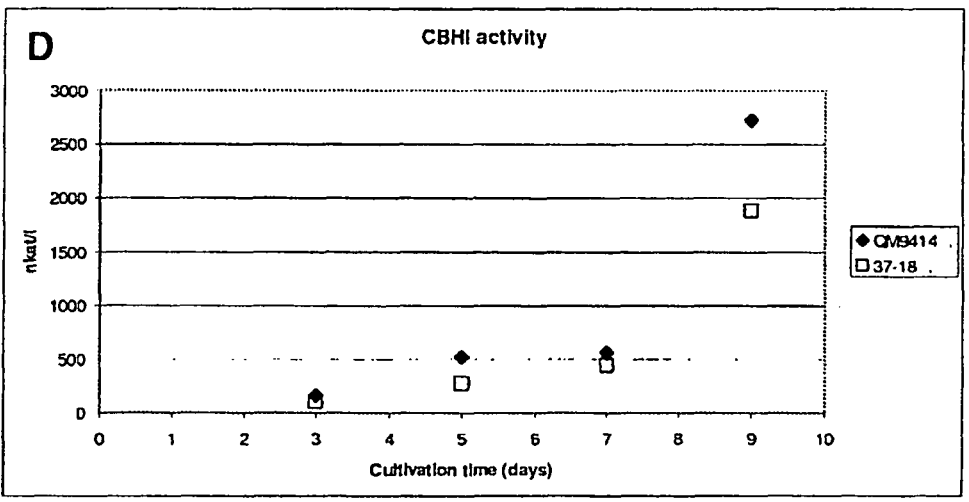
Figure 2:
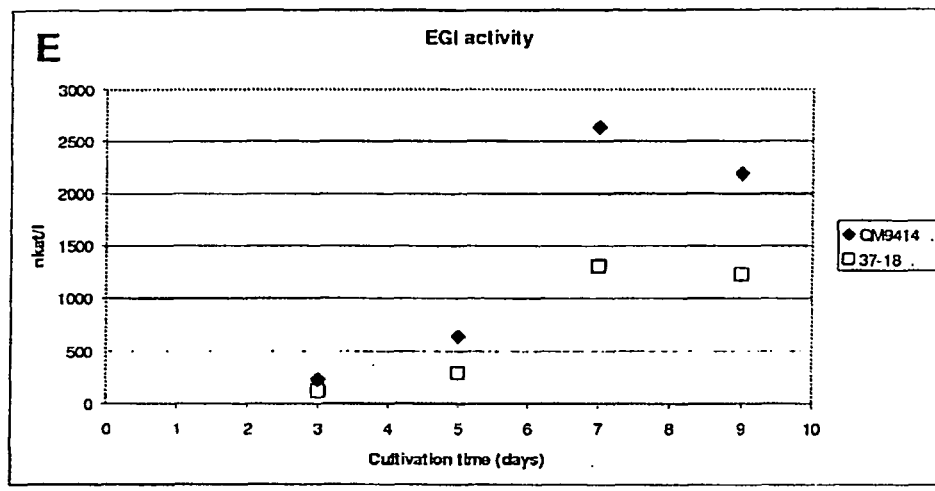
Figure 2:
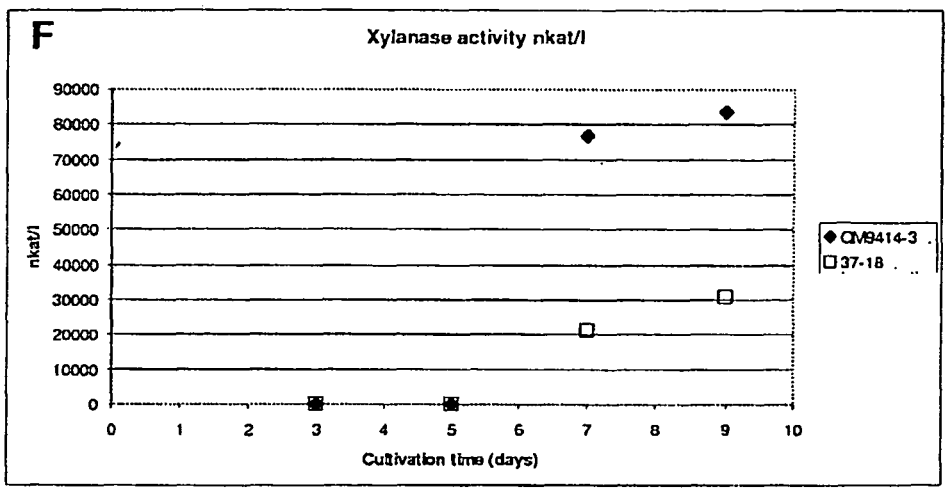
Figure 2:
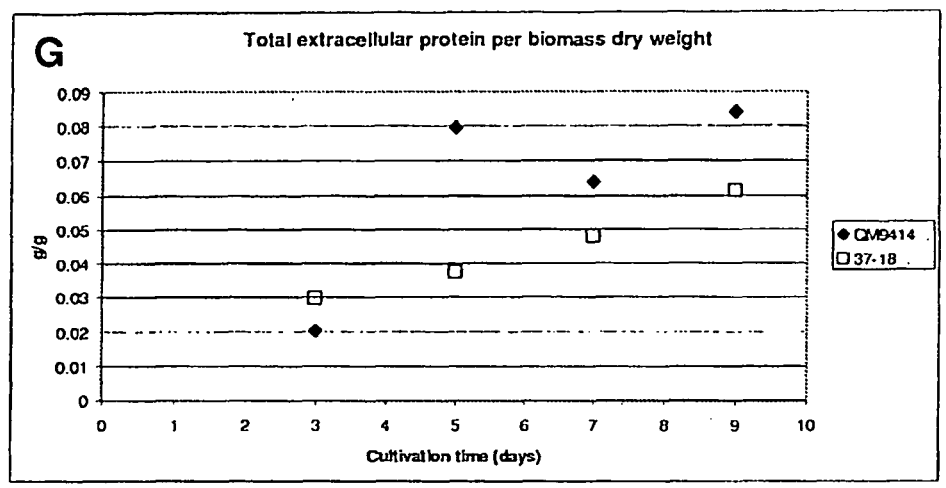
Figure 2:
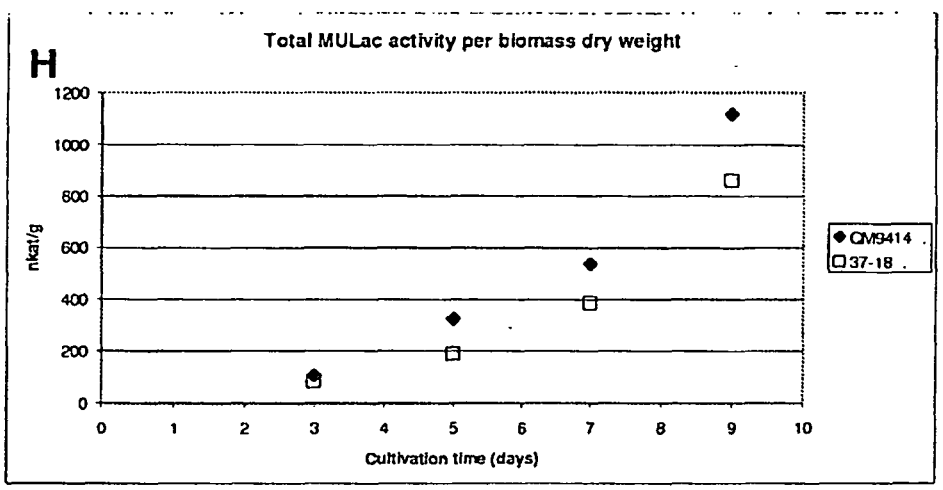
Figure 2:
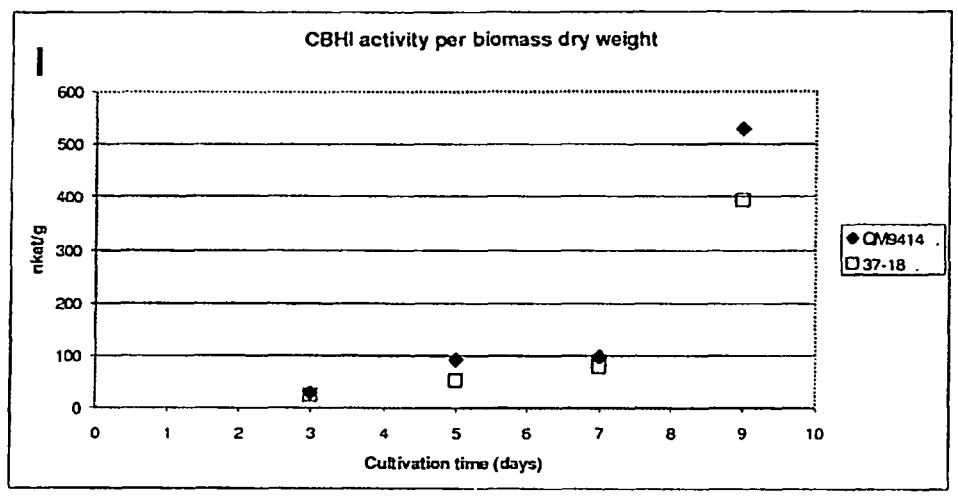
Figure 2:
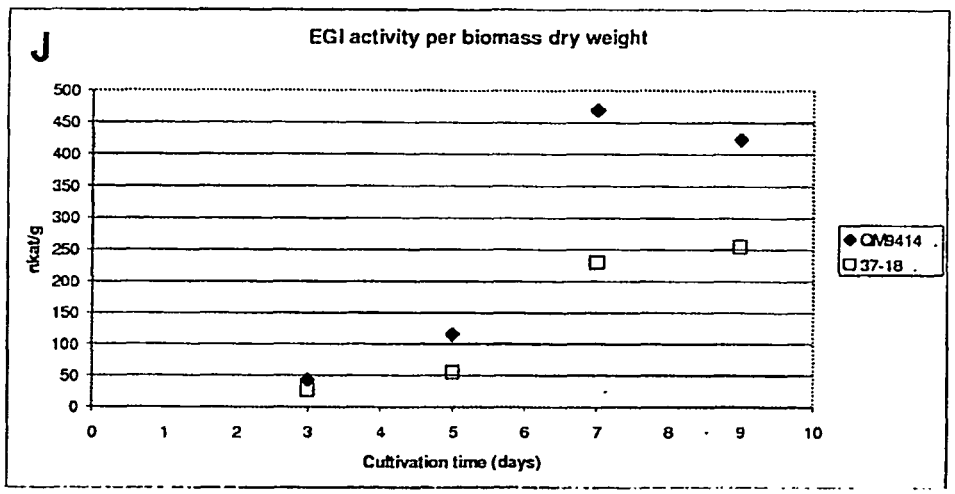
Figure 2:
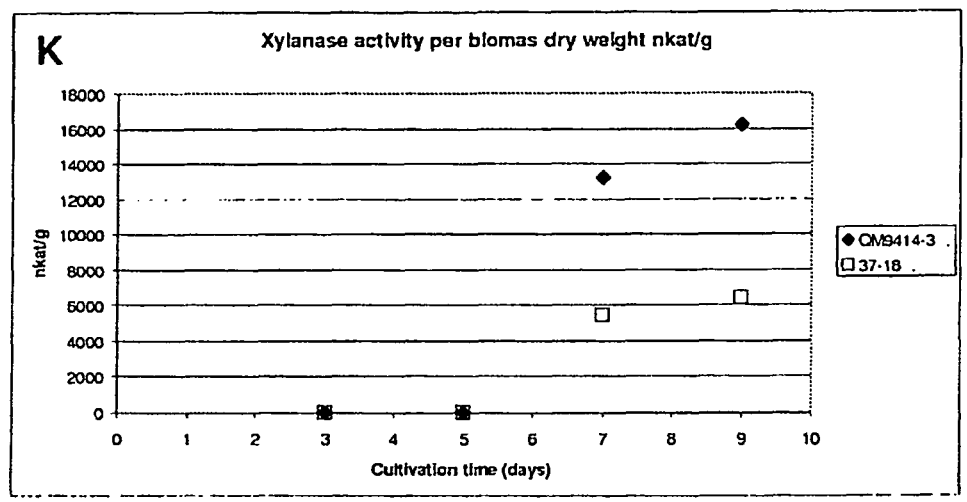

The effect of gene tre81972 (FIG. 2), represented by SEQ ID NO:2, was exemplified by constructing strain *T. reesei*

37-18 overexpressing the gene. The overexpression of the gene had a negative effect on protein production. The overexpression strain 37-18 produced less total extracellular protein, less cellulase activity (measured as total MULac or CBHI activity or especially as EGI activity) and hemicellulase activity (measured as activity on xylan substrate). Inactivation of the gene tre81972 is expected to remove the negative effect on protein production, and inactivation of the gene is expected result in improved production of cellulases, hemicellulases, other secreted proteins, or heterologous proteins produced under cellulase or hemicellulase gene promoters.

Figure 3:
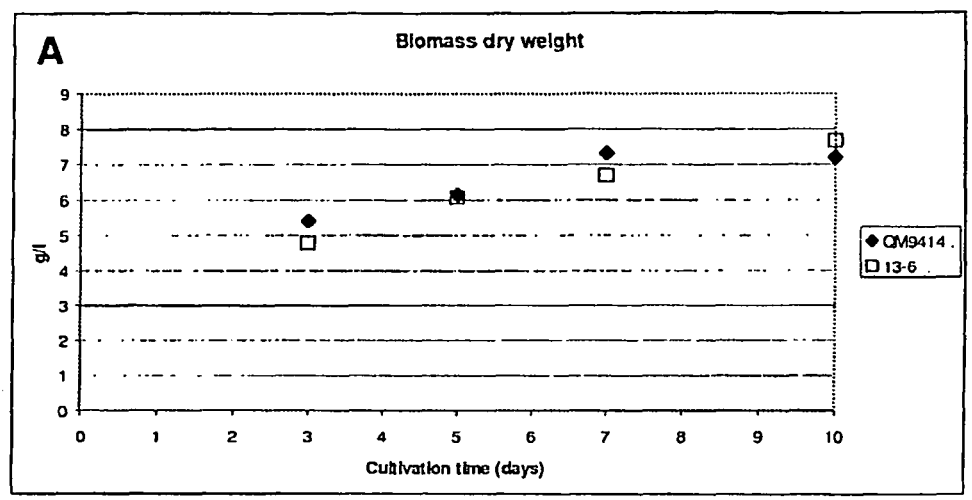
Figure 3:
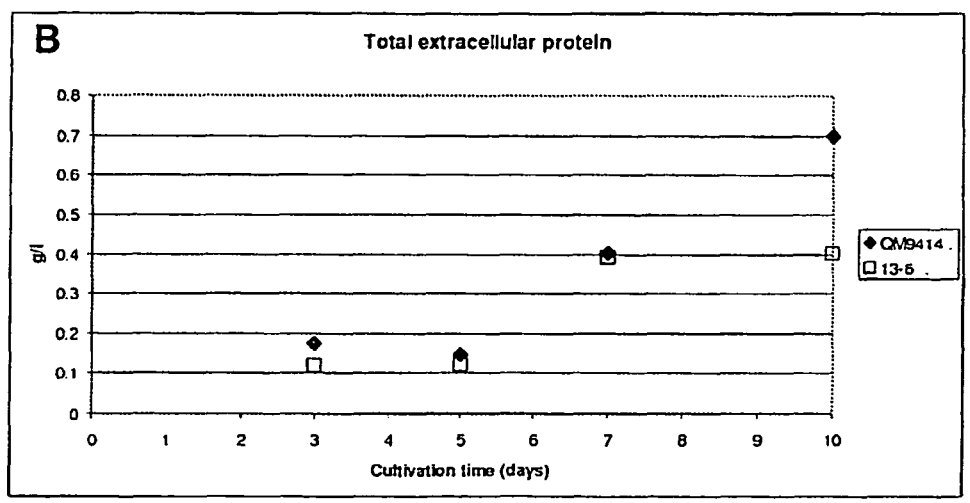
Figure 3:
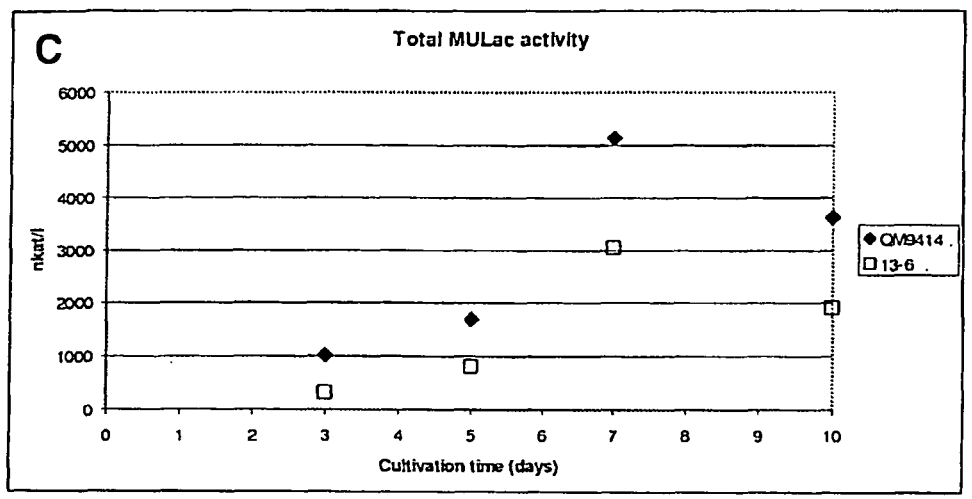
Figure 3:
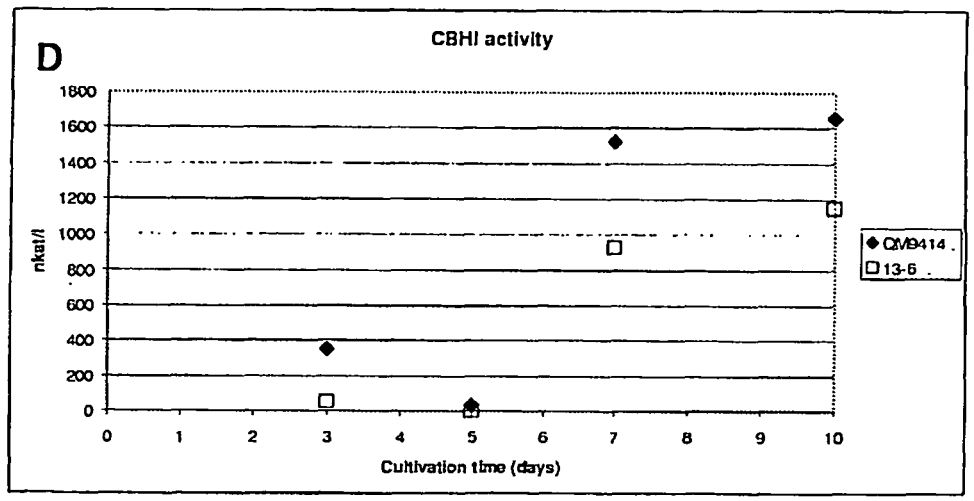
Figure 3:
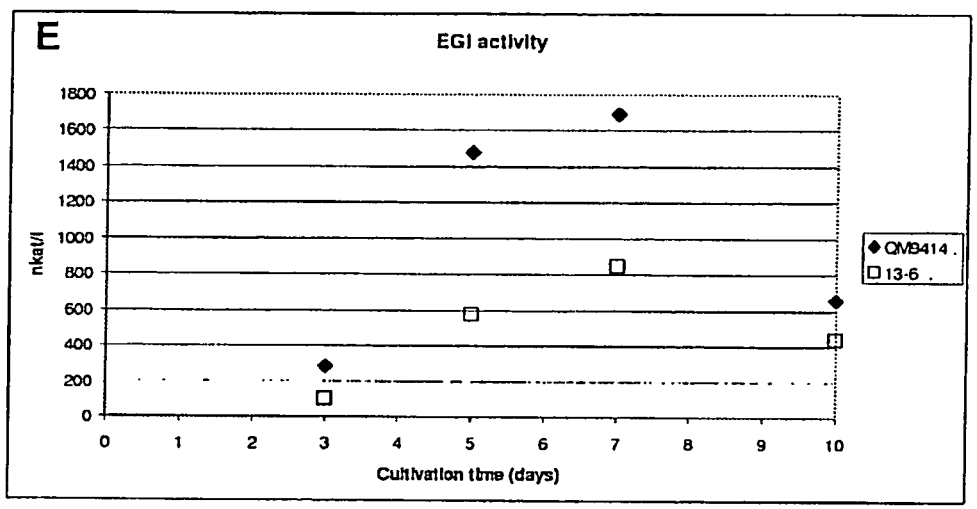
Figure 3:
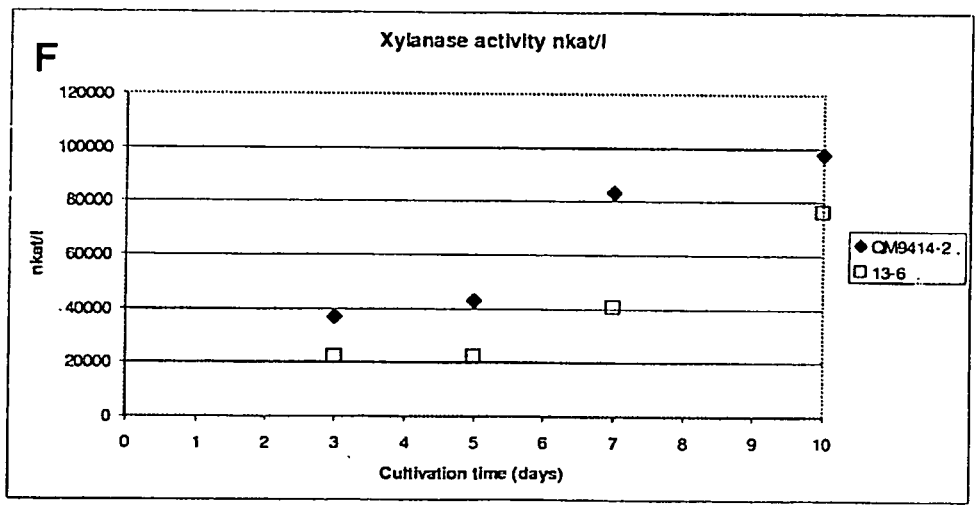
Figure 3:
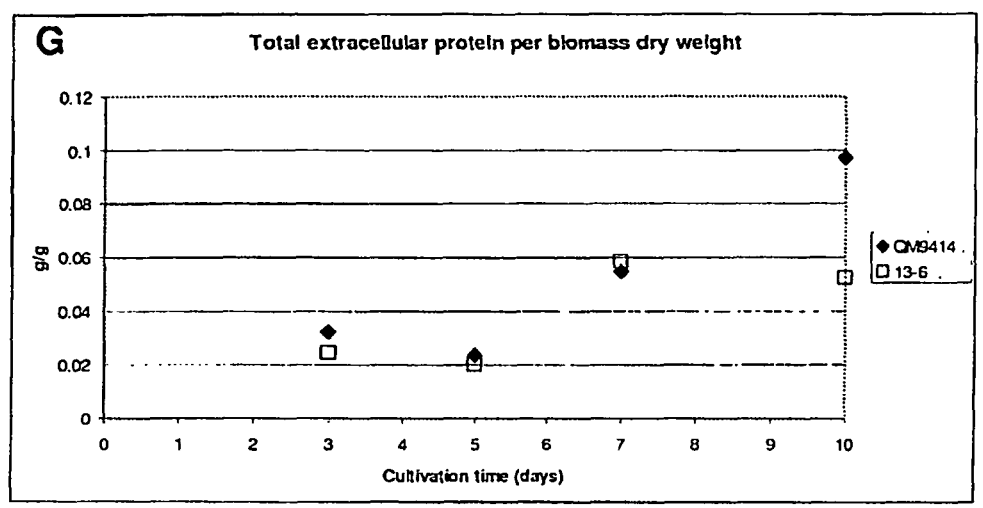
Figure 3:
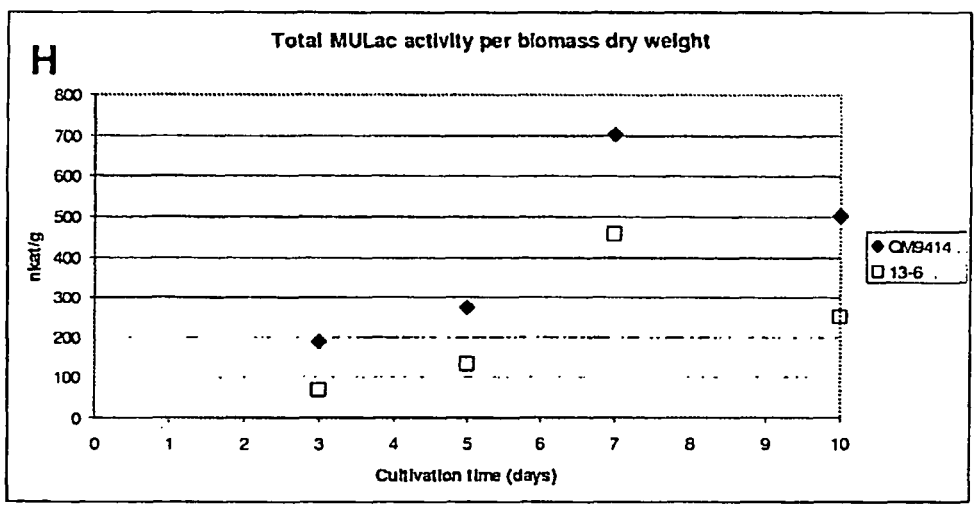
Figure 3:
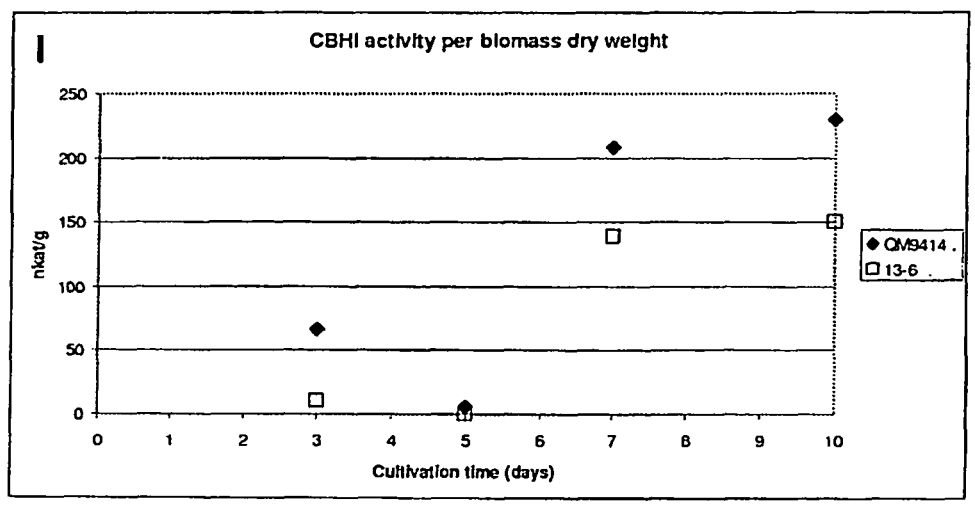
Figure 3:
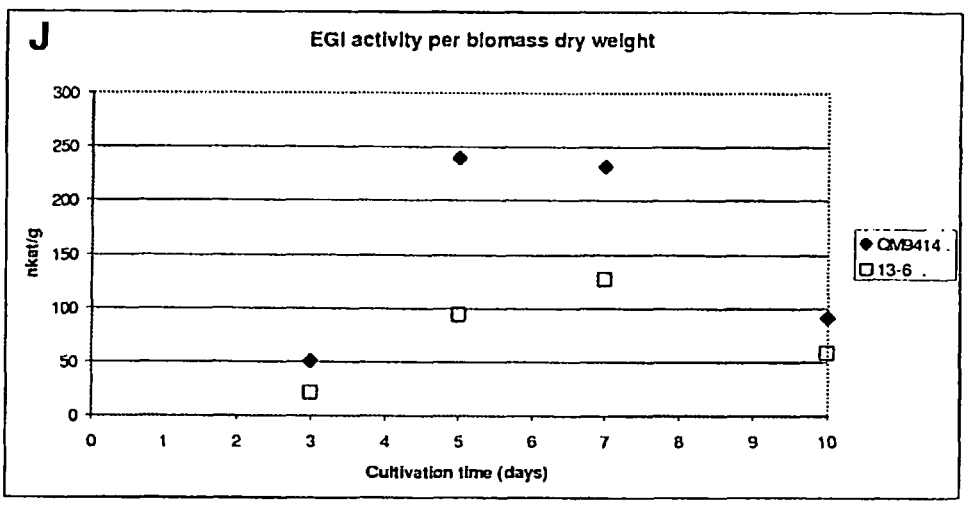
Figure 3:
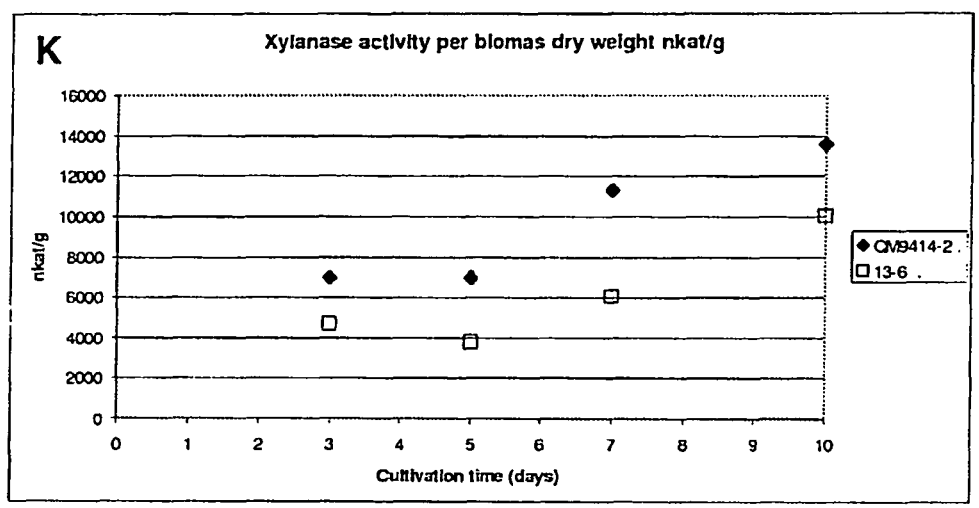

The effect of gene tre62244 (FIG. 3), represented by SEQ ID NO:3, was exemplified by constructing strain T. reesei 13-6 overexpressing the gene. The overexpression had negative effect on production of cellulases and hemicellulases. The overexpression strain 13-6 produced less cellulase activity (measured as total MULac activity or CBHI or EGI activity) and hemicellulase activity (measured as activity on xylan substrate) as compared to the parent host strain. However, the total amount of extracellular protein produced by the strain was not lower than that of the parent host strain until the final stage of the cultivation. The result indicates that the strain 13-6 produced increased amount of some other proteins than the cellulases, CBHI, EGI or BGL, or enzymes active on the xylan substrate. Gene tre62244 should be deleted in order to enhance cellulase or hemicellulase production or heterologous protein production under cellulase or hemicellulase gene promoters. However, overexpression of the gene 62244 may be beneficial for production of other secreted proteins than the cellulases, CBHI, EGI or BGL, enzymes active on the xylan substrate.

Figure 4:
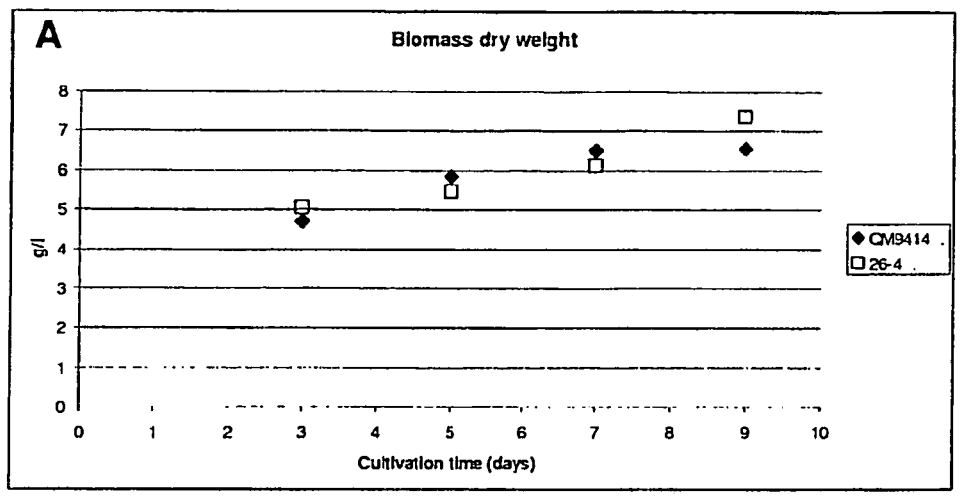
Figure 4:
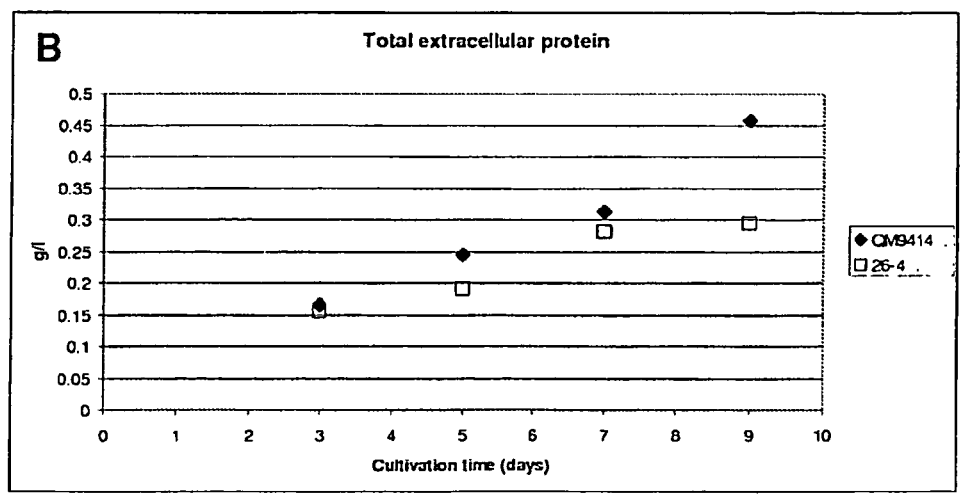
Figure 4:
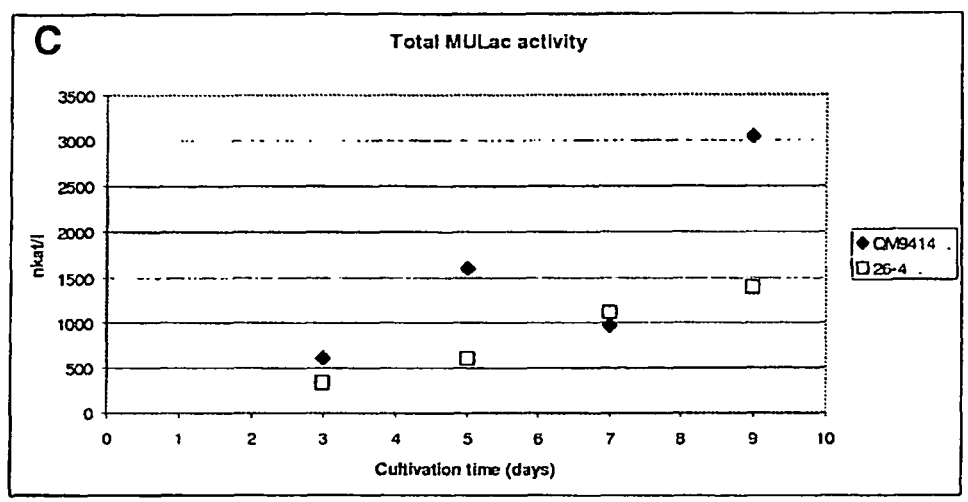
Figure 4:
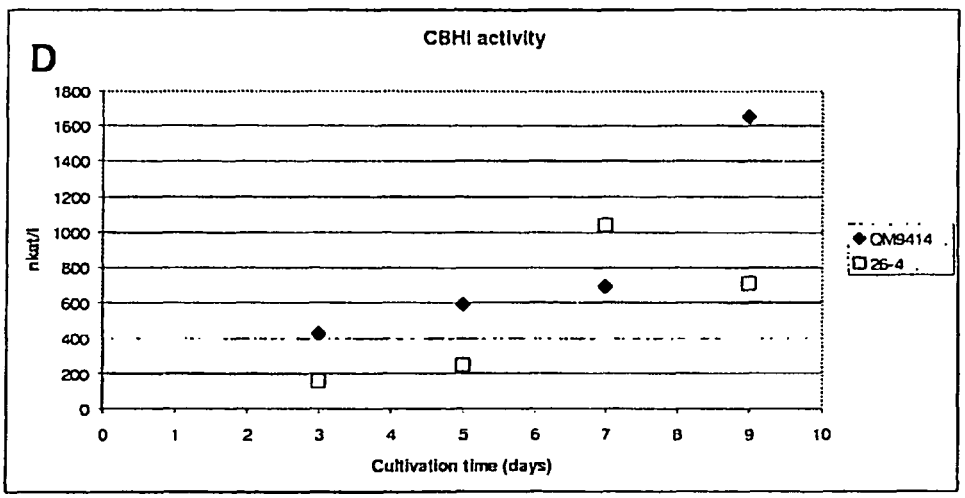
Figure 4:
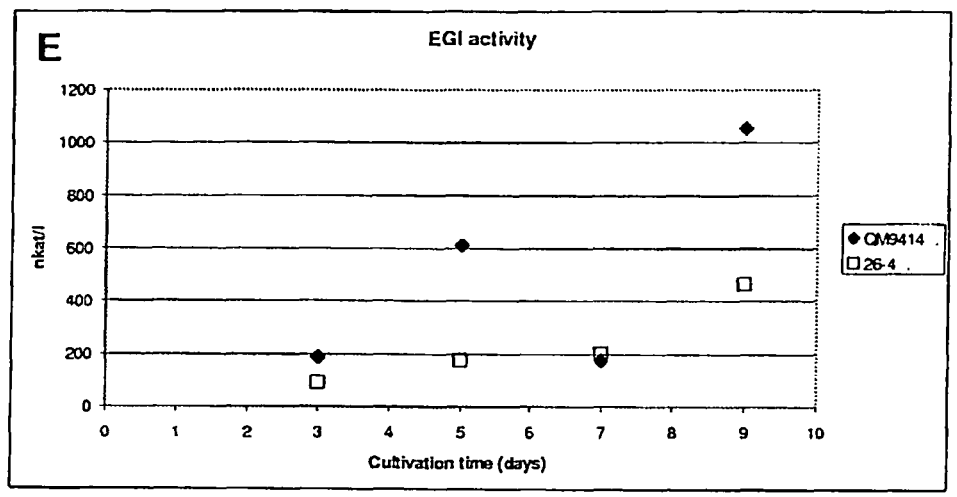
Figure 4:
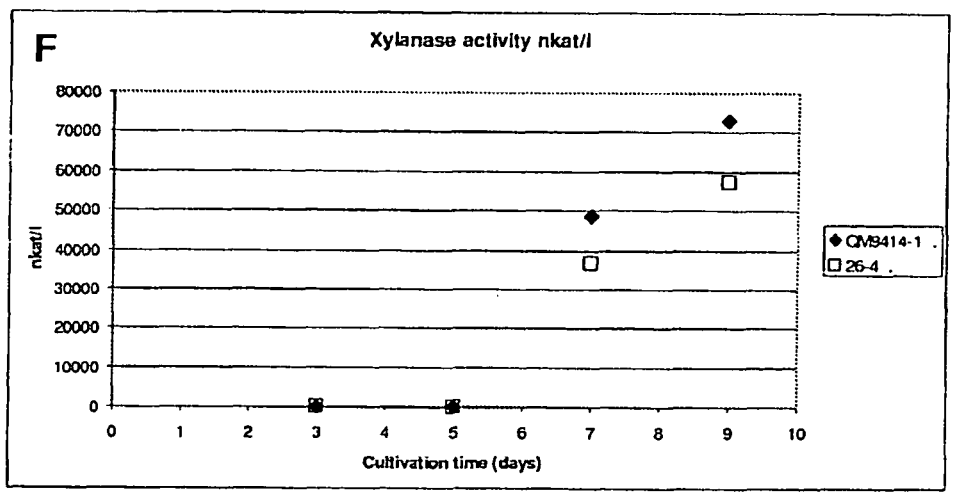
Figure 4:
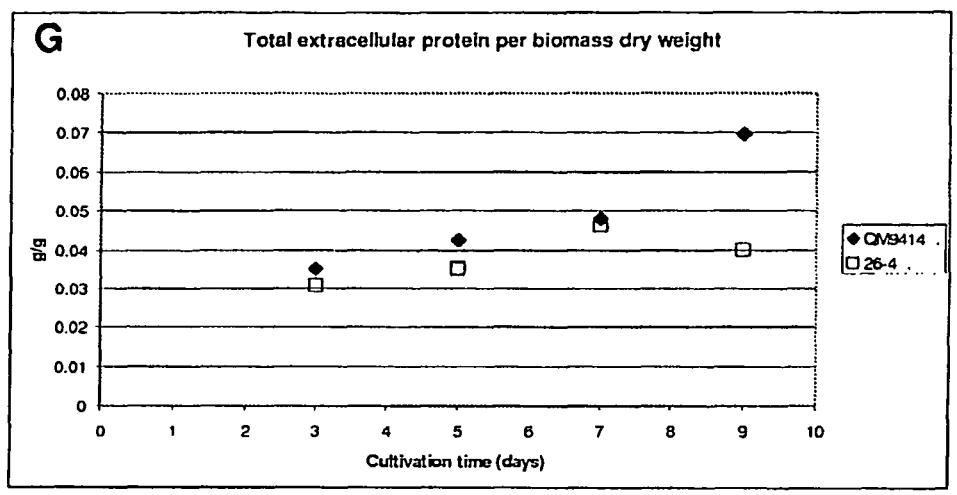
Figure 4:
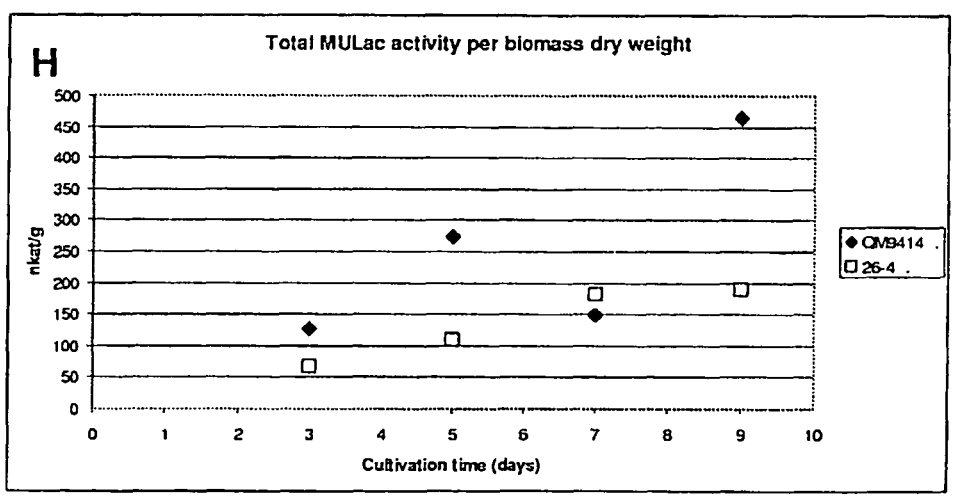
Figure 4:
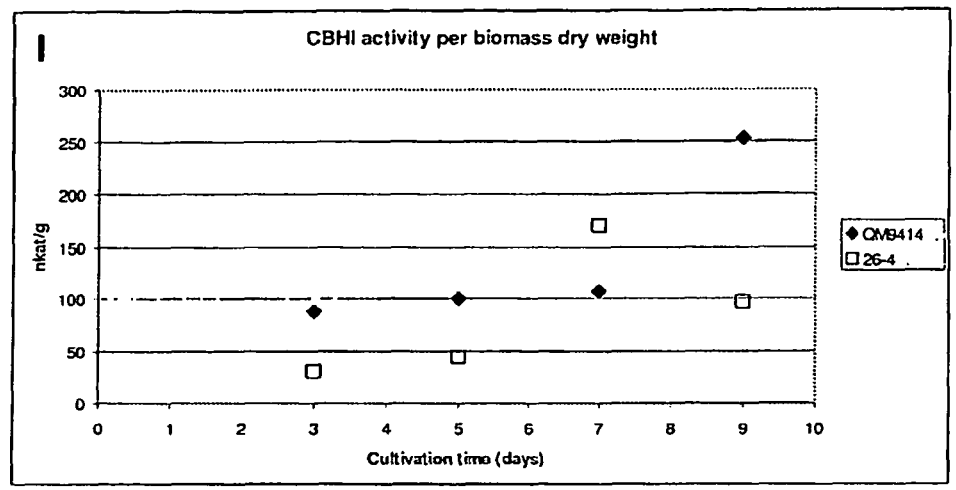
Figure 4:
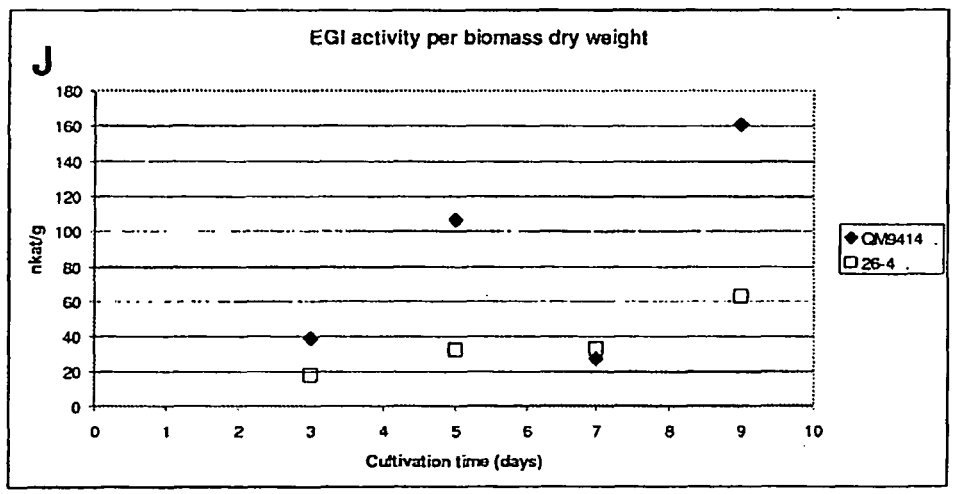
Figure 4:
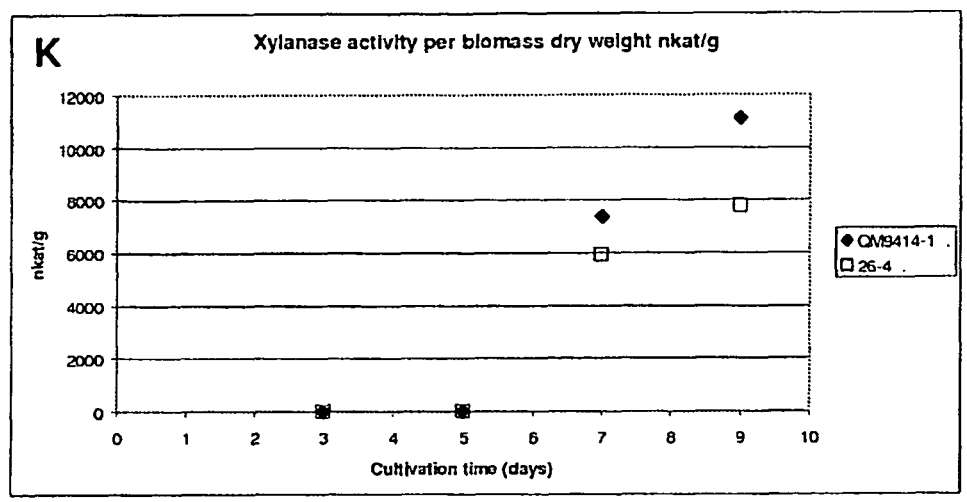

The effect of gene tre76677 (FIG. 4), represented by SEQ ID NO:4, was exemplified by constructing strain T. reesei 26-4 overexpressing the gene. The overexpression of this gene had a negative effect on production of secreted proteins. Overexpression of the gene caused decreased production of cellulase activity, measured as total MULac, CBHI or EGI activity, decreased production of hemicellulase activity, measured as xylanase activity, as well decreased production of total extracellular protein. The maximal level of the proteins and enzyme activities produced were lower in the cultures of the strain overexpressing the gene tre76677 as compared to the cultures of the parent host. The gene tre76677 should be deleted to remove the negative effect on protein production, including cellulase and hemicellulase production or production of other secreted proteins or heterologous protein production under promoters of cellulase or hemicellulase genes.

Figure 5:
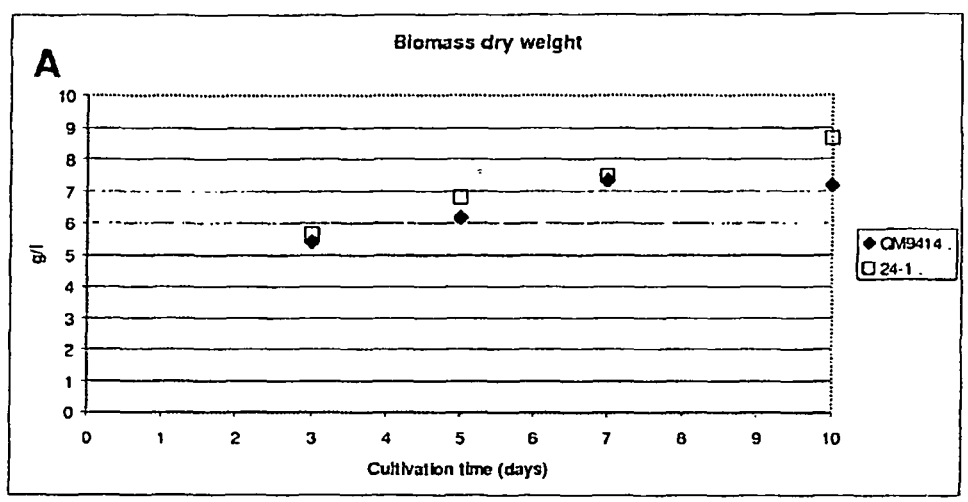
Figure 5:
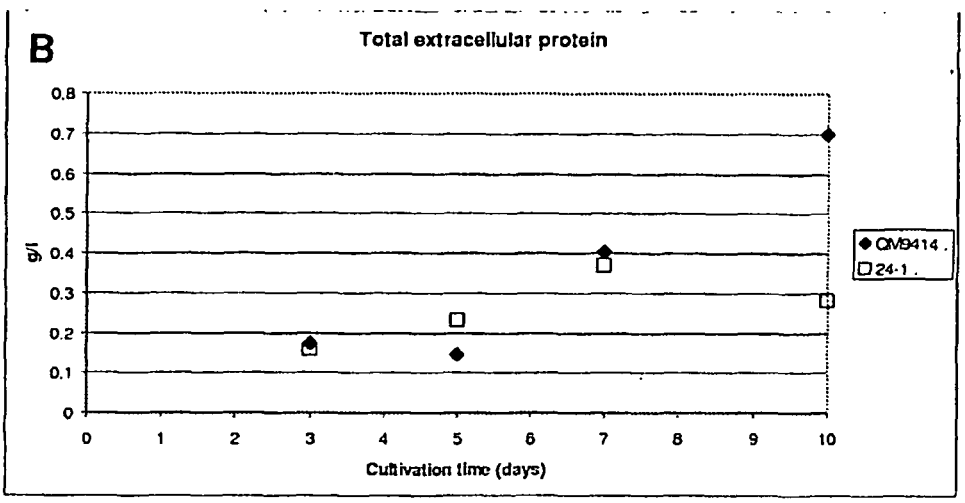
Figure 5:
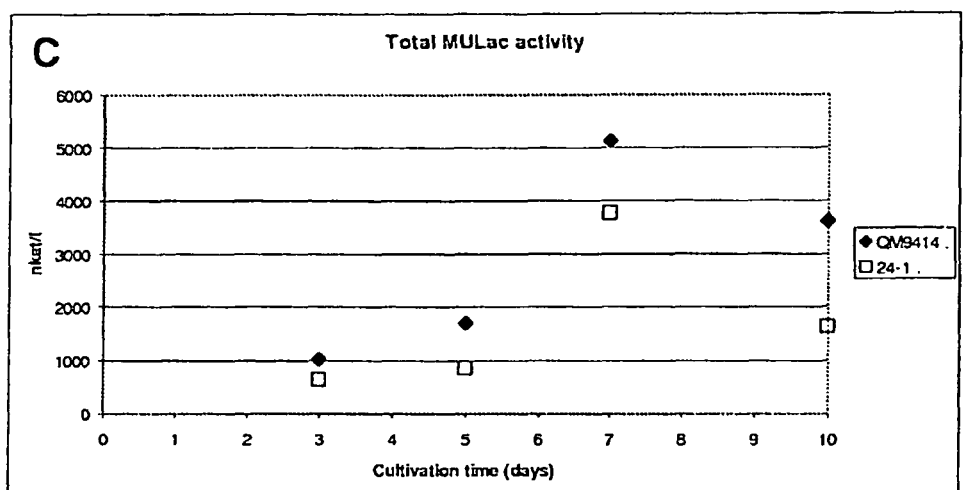
Figure 5:
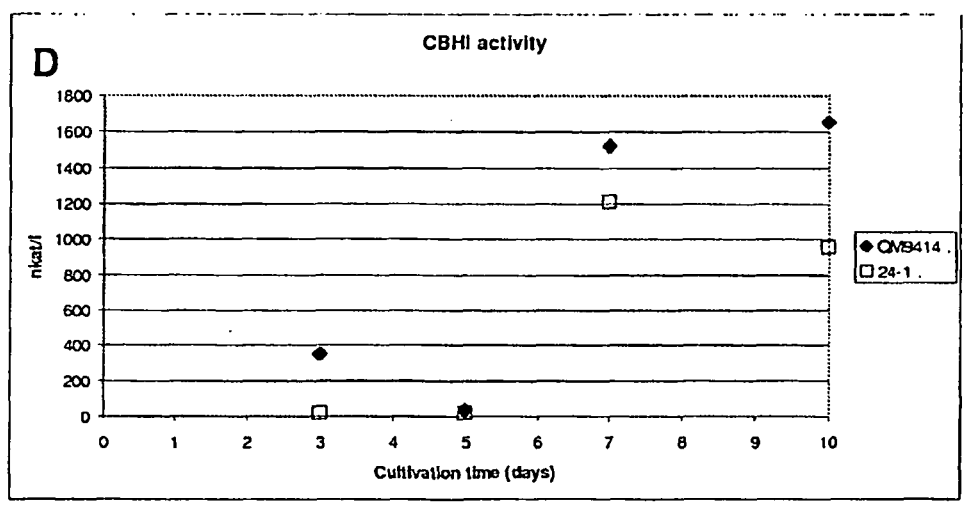
Figure 5:
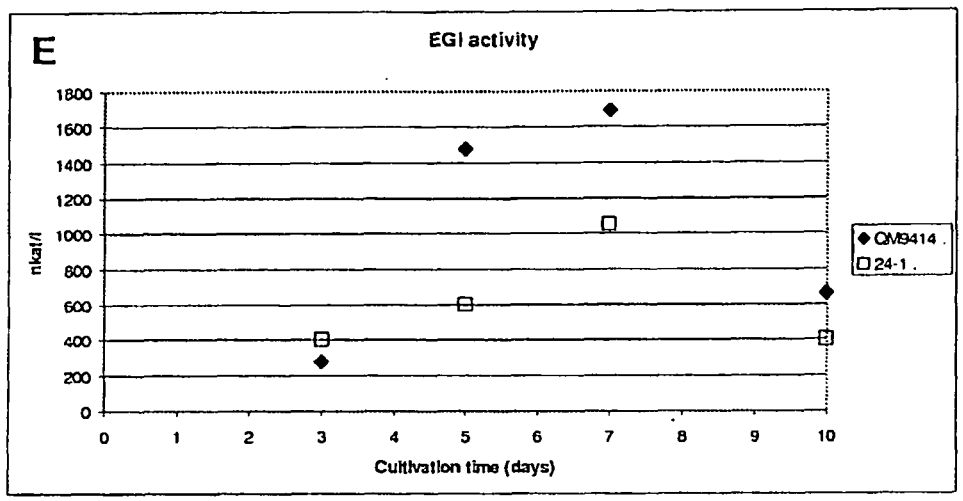
Figure 5:
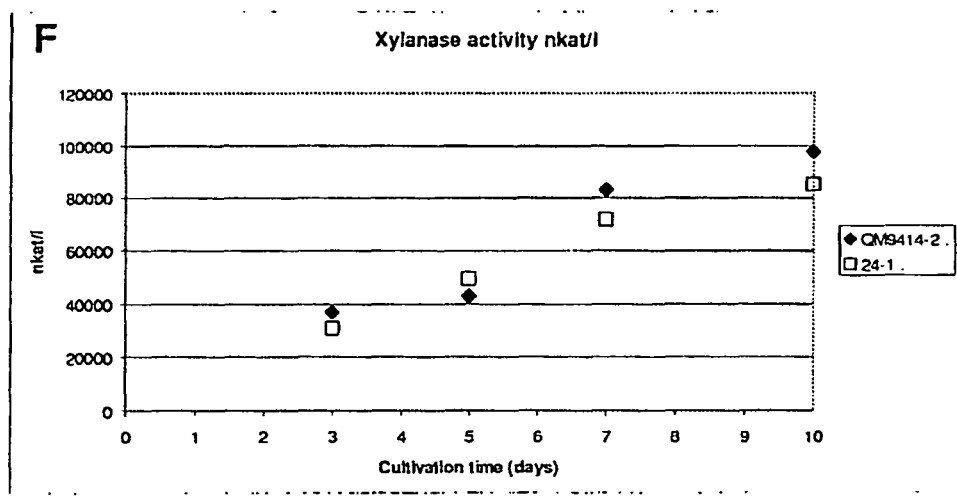
Figure 5:
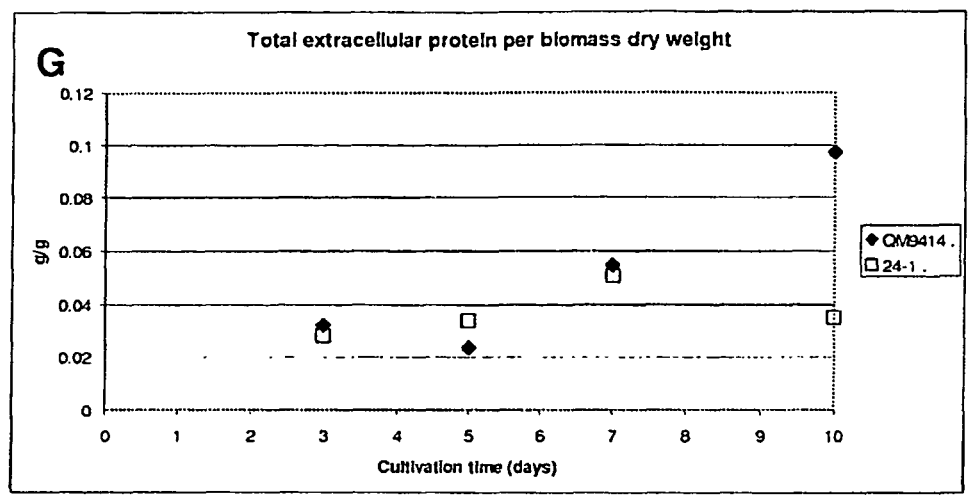
Figure 5:
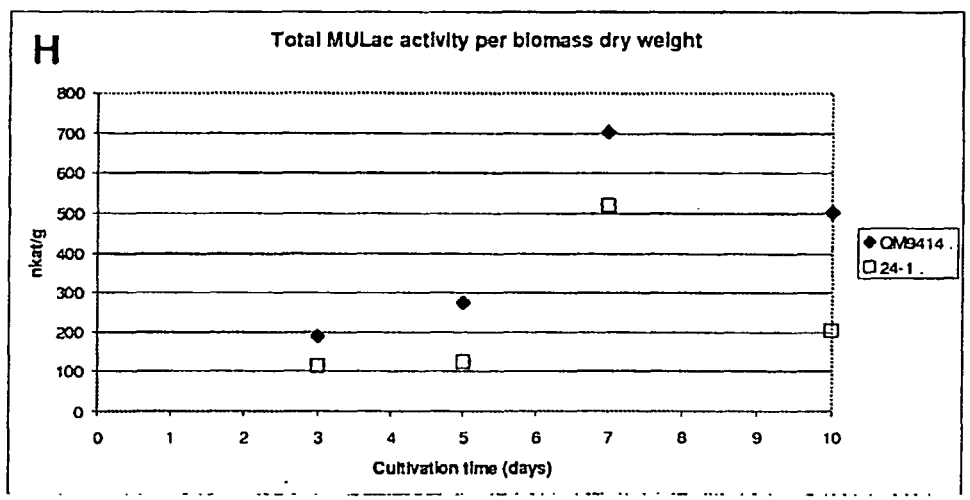
Figure 5:
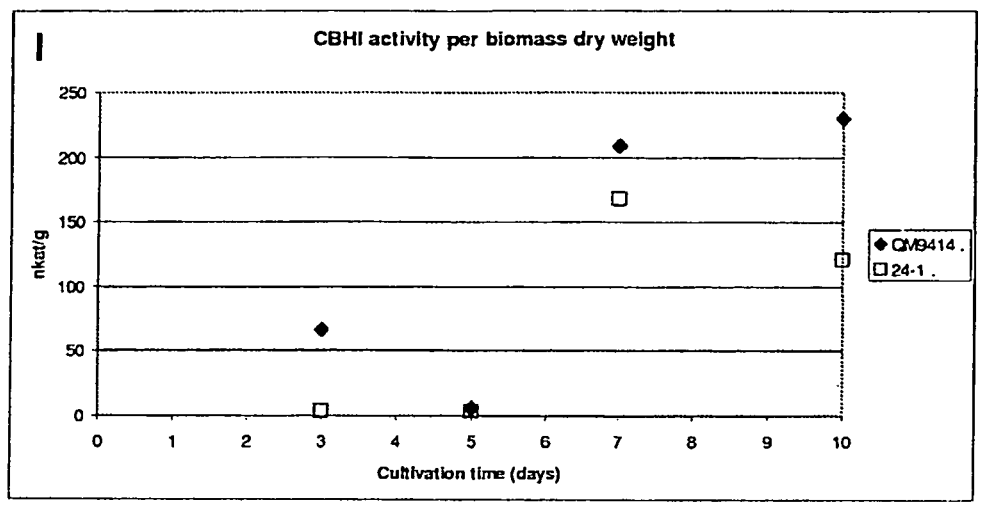
Figure 5:
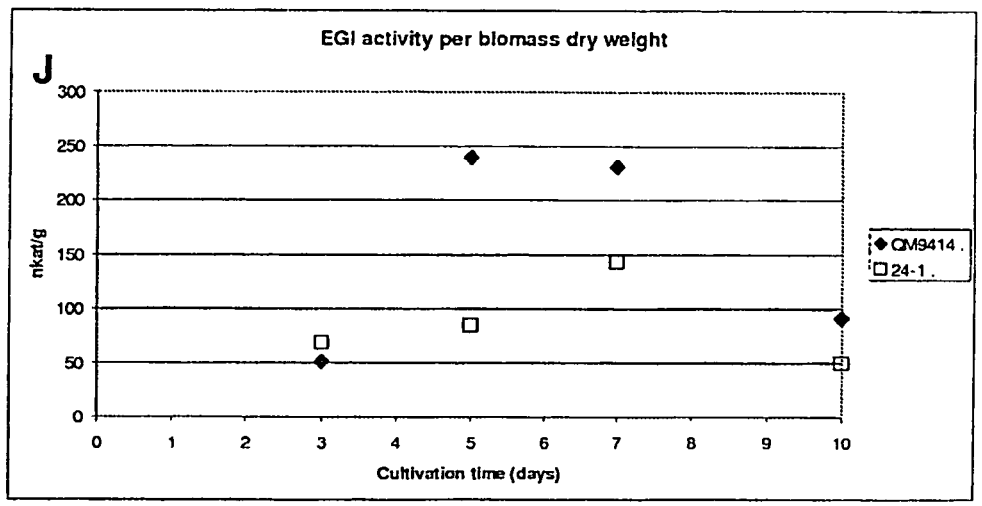
Figure 5:
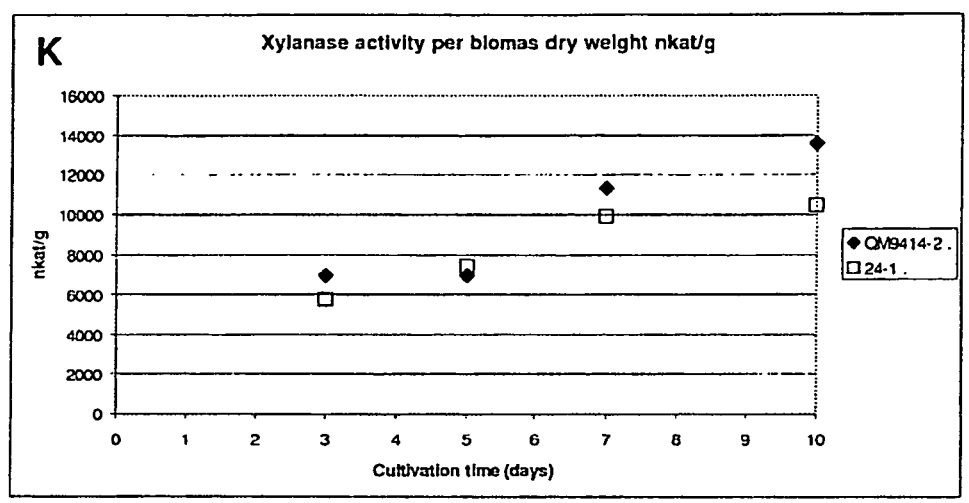
Figure 6A:
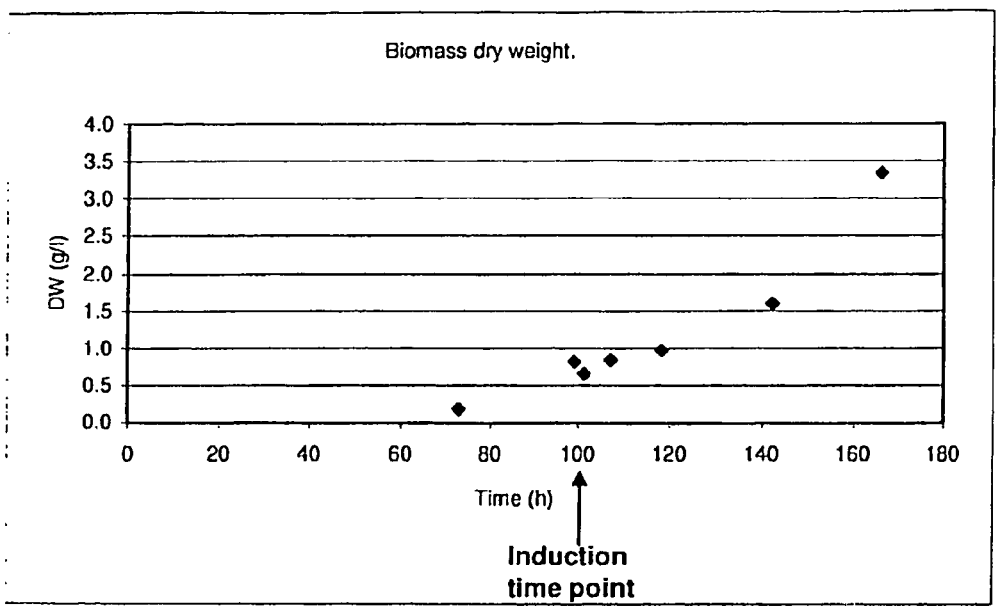
FIG. 6A Biomass (g/l) in *T. reesei* precultures before induction of hydrolytic enzyme production and in the uninduced control cultures at the sampling time points of the induction experiment.
Figure 6B:
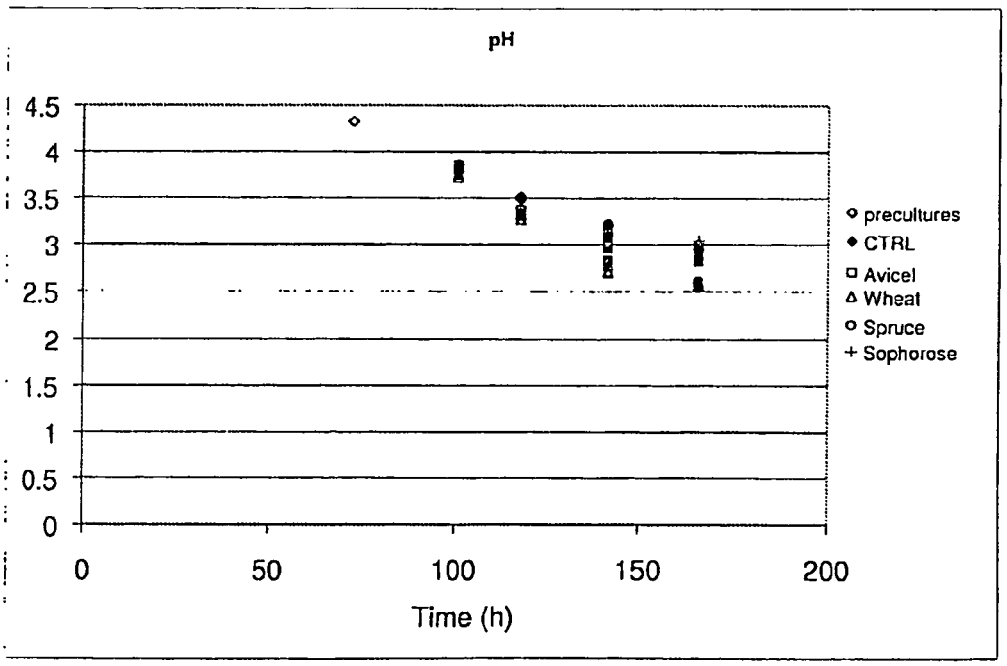
FIG. 6B pH of the *T. reesei* cultures induced either with Avicel, spruce, wheat straw or sophorose, as well as the precultures before induction and the uninduced control cultures.

The effect of gene tre47317 (FIG. 5), represented by SEQ ID NO:5, was exemplified by constructing strain T. reesei 24-1 overexpressing the gene. The overexpression of the gene had negative effect on production of secreted proteins. The cultures of the strain 24-1 produced less cellulase activity, measured as total MULac, CBHI or EGI activity, as well as hemicellulase activity, measured as xylanase activity, as compared to the cultures of the parent host. However, the production of total extracellular protein did not show significant decrease in the strain 24-1 cultures as compared to the parent host. The result indicates that the strain 24-1 produced increased amount of some other proteins than the cellulases, CBHI, EGI or BGL, or enzymes active on the xylan substrate. The gene tre47317 should be deleted in order to enhance cellulase or hemicellulase production or heterologous protein production under cellulase and hemicellulase gene promoters. Overexpression of the gene tre47317 is expected toenhance production of other proteins than CBHI, EGI or BGL or the enzymes active on the xylan substrate. The gene should be deleted also to reduce carbon consumption for biomass production.

The effect of the genes as described herein has been exemplified by overexpressing them in *Trichoderma*. The strain was *T. reesei* QM9414 (ATCC 26921), which is generally available to the public.

Total Mulac is measured as enzyme activity against Mulac substrate measuring activities of CBHI, EGI, and BGL.

EGI has been measured as enzyme activity against Mulac in the presence of glucose, to inhibit BGLI, and cellobiose, to inhibit the activity of CBHI.

CBI-II has been measured as enzyme activity against Mulac obtained by subtracting the activity measured in the presence of glucose and cellobiose from the activity measured in the presence of glucose and in the absence of cellobiose.

The methods for determing cellulase activities has been described in Bailey and Tahtiharju, 2003; Collen et al., 2005; van Tilbeurgh et al., 1982, 1985, 1988.

EXAMPLES

Example 1

Cultivation of *Trichoderma reesei* for Transcriptome Analysis to Study the CelluLar Responses During Induction of Hydrolytic Enzyme Production Cultivation Procedure

*Trichoderma reesei* Rut-C30 (ATCC56765) was cultivated in shake flasks in medium containing 7.6 g/l $(NH_4)_2SO_4$, 15.0 g/l $KH_2PO_4$, 2.4 mM $MgSO_4.7H_2O$, 4.1 mM $CaCl_2.H_2O$, 3.7 mg/l $CoCl_2$, 5 mg/l $FeSO_4.7H_2O$, 1.4 mg/l $ZnSO_4.7H_2O$, 1.6 mg/l $MnSO_4.7H_2O$, and 10 g/l sorbitol. pH of the medium was adjusted to 4.8 by addition of KOH. The cultures were inoculated with $8\times10^7$ spores/200 ml medium and grown for 4 days in conical flasks at 28° C. with shaking at 250 rpm. For induction of the hydrolytic enzyme production, the cultures were combined and aliquots of the combined culture transferred to flasks containing inducing medium (200 ml of the culture per 90 ml of the inducing medium). The composition of the inducing medium was as described above except for containing 2 g/l sorbitol and supplemented either with Avicel cellulose, pretreated wheat straw, pretreated spruce or sophorose. Uninduced control cultures were treated similarly except that no supplement was used in the inducing medium. The concentrations of the inducing substances were 1% (w/v) of Avicel, wheat or spruce or 0.7 mM sophorose. Pretreatment of spruce and wheat straw was done using steam explosion, followed by washing steps. The fibrous fraction of the material was used for the induction.

Collection of Samples and Sample Treatment

Samples for analysis of biomass production, pH of the culture supernatant, and for RNA isolation were collected at different time points during the pre-cultivation step as well as from the combined culture before induction. After addition of the inducing substances the cultures were sampled for pH measurement and RNA isolation; biomass formation was measured only from separate uninduced control flasks reserved for the purpose. The sampling time points of the induced cultures were Oh, 6 h, 17 h, and 41 h after the onset of induction. Biomass dry weight was measured by filtering and drying mycelium samples at 105° C. to constant weight (24 h). For RNA isolation mycelium samples of 50 ml were filtered, washed with equal volume of 0.7% (w/v) NaCl, frozen immediately in liquid nitrogen, and stored at −80° C. Total RNA was isolated using the Trizol™ Reagent (Gibco BRL) essentially according to manufacturer's instructions, and purified further by column purification (Qiagen, manufacturer's instructions). cDNA was synthesised from the purified RNA, followed by fluorescent labelling and expression microarray analysis using custom oligonucleotide microarrays by Roche NimbleGen, Inc. The design for the microarray probes and slides was done according to *T. reesei* genome version v2.0.

Monitoring of the Cultures

Figure 7A:
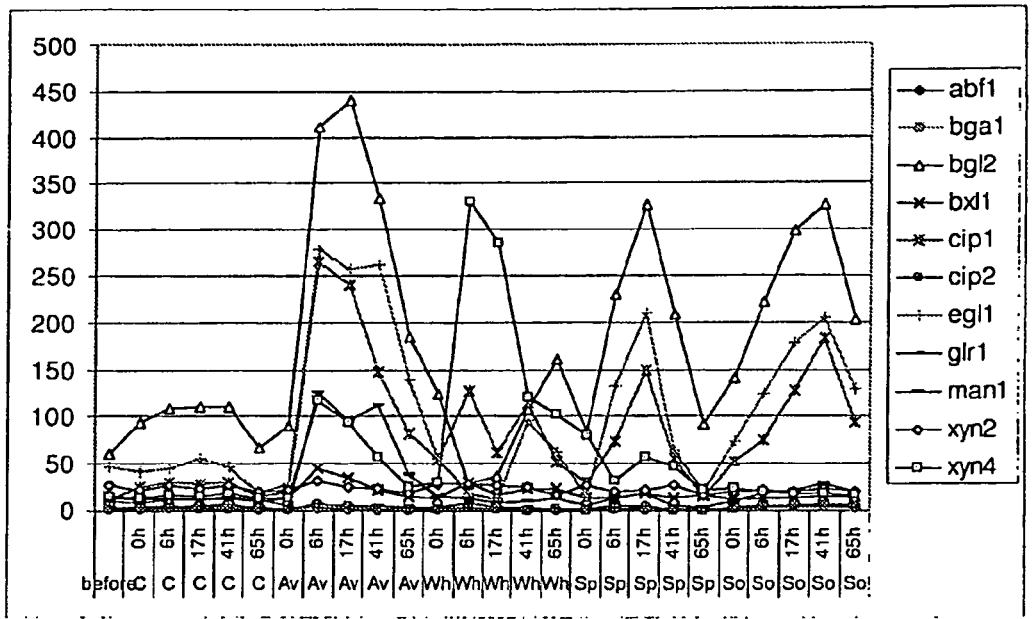
FIG. 7A. Transcript levels of a set of known genes encoding hydrolytic enzymes during an induction experiment: abf1 (arabinofuranosidase 1), bga1 (beta-galactosidase 1), bgl1 (beta-glucosidae 1), bxl1 (beta-xylosidase 1), cip1 (cellulose-binding), cip2 ( ) eg11 (endoglucanase 1), girl (glucuronidase 1), man1, xyn2 and xyn4.
Figure 7B:
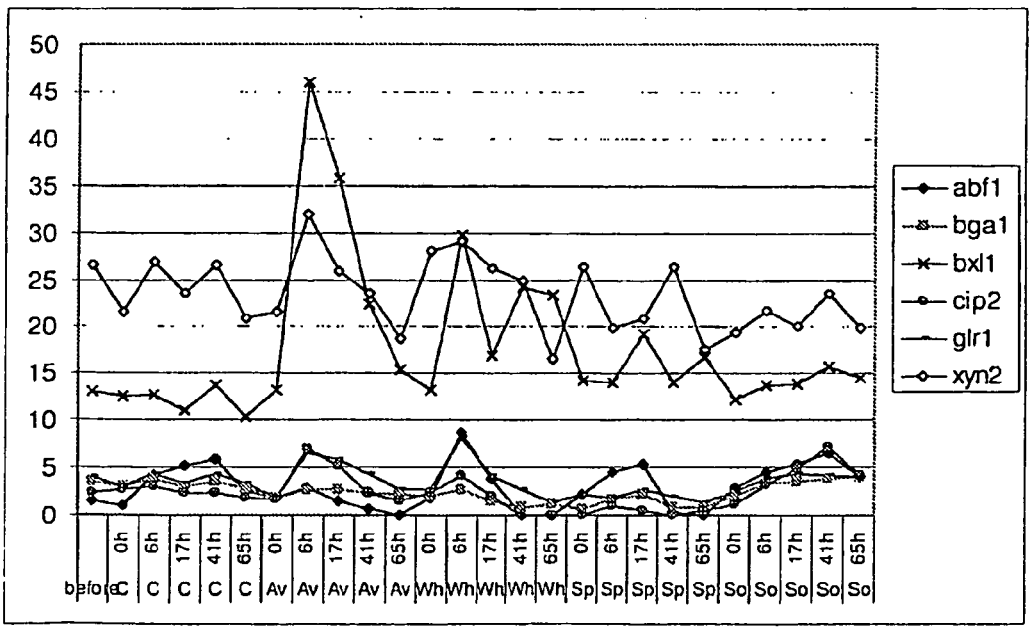
FIG. 7B Transcript levels of a set of known genes encoding hydrolytic enzymes during an induction experiment: abf1 (arabinofuranosidase 1), bga1 (beta-galactosidase 1), bxl1 (beta-xylosidase 1), cip2 ( ) girl (glucuronidase 1), and xyn2.

During the precultivation stage the progress of the cultivations was monitored by analysis of biomass formation and change of pH in the culture supernatant. After the onset of the induction biomass formation was only measured from uninduced control cultures specifically dedicated for the purpose, since the insoluble material in the inducing media could not be seoarated from fungal biomass. pH was measured from all the cultures throughout the cultivation procedure. Biomass dry weight (g/l) in the precultures before induction and in the uninduced contol cultures are sgown in FIG. 7A and pH of the cultures in FIG. 7B. The biomass and pH data show that, at the induction time point 100 h, the cultivations were actively growing and growth continued during the induction time period in the control cultures. The extent of pH decrease in the cultures during time suggest equal growth characteristics of the replicate cultures. No significant difference was detected between the uninduced and sophorose induced cultures either. In cultures with Avicel, the pH decreased slightly faster as compared to the uninduced culture, and the cultures with spruce and wheat showed fastest decrease in the pH, the difference being, however, relatively small.

Example 2

TRAC Analysis of a Selected Set of Genes Encoding Hydrolytic Enzymes

In order to select the optimal time points of the induction experiment for the expression microarray analysis, transcription levels of a set of known genes encoding hydrolytic enzymes were analysed using TRAC method. The relative expression levels are shown for abf1 (arabinofuranosidase 1), bga1 (beta-galactosidase 1), bgl1 (beta-glucosidase 1), bxl1 (beta-xylosidase 1), cip1 (cellulose-binding), cip2 ( ) egl1 (endoglucanase 1), girl (glucuronidase 1), man1, xyn2 and xyn4. Clear induction was detected for majority of the genes at the time points 6 h and 17 h, and also at 41 h of the sophorose cultures, and these time points were selected for the microarray analysis. The transcript levels detected by the TRAC analysis are shown in FIG. 8A and FIG. 8B.

Example 3

Expression Microarray Analysis of the Induced Cultures

The cultures induced either with Avicel, sophorose, pretreated wheat straw or pretreated spruce were subjected to microarray expression analysis. The time points Oh, 6 h, 17, and 41 h of the uninduced and sophorose induced cultures were used for the analysis, and the time points Oh, 6 h and 17 h were selected for the Avicel, wheat and spruce induced cultures. The microarray analysis was done using custom oligonucleotide microarrays by Roche NimbleGen, Inc. The design for the microarray probes and slides was done according to *T. reesei* genome version v2.0. Raw microarray data was analysed using R and the Bioconductor packages Oligo, Limma and Mfuzz.

The analysis showed co-expression of a group of genes together with cellulase or hemicellulase genes. These genes included novel previously not described genes with sequence domains typical to genes for different types of regulatory proteins, including genes for transcription factors, kinases, and proteins involved in histone modification and chromatin remodelling. In order to evaluate the effect of these genes on protein production, and specifically production of hydrolytic enzymes, like cellulases and hemicellulases, a set of these genes were cloned and overexpressed in *T. reesei* QM9414 (ATCC 26921). The selected genes had a significantly higher expression at least in three of the inducing conditions studied as compared to the unincuced cultures at the same time point, or that the expression profile of the genes was similar to the expression profiles of known hemicellulase or cellulase genes (according to M fuzz clustering of the expression data). The selected genes with their corresponding protein identity number, predicted functional prediction based on the sequence domains, and information on their induction in the presence of different inducing substances at different time points of the induction experiment are listed in Table 3.

The information provided on the genes include the ID number according to JGI genome version 2.0, predicted function of the gene based on the sequence data, and data on induction of the gene in the presence of different inducers (Avicel, pretreated wheat straw, pretreated spruce or sophorose) at different induction time points. Statistically significant induction (higher expression level as compared to the uniniduced control cultures at the same time point) in the Avicel, Spruce, Wheat or Sophorose induced cultures at the time points Oh, 6 h, 17 h, or 41 h is indicated by "1", and statistically significant reduction in the expression level by "−1".Table 3. The induced genes encoding putative regulatory factors and selected fro overexpression in T. reeseL

TABLE 3

The induced genes encoding putative regulatory factors and selected for overexpression in *T. reesei*.

| | | | Inducer | | | | |
|---|---|---|---|---|---|---|---|
| | | | Avicel | Avicel | Avicel | Wheat | Wheat |
| | | | | | Time (h) | | |
| Gene ID | Class | Extension | 0 h | 6 h | 17 h | 0 h | 6 h |
| TRIRE0108381 | Regulation | Transcription factor | 0 | 1 | 1 | 0 | 1 |
| TRIRE081972 | Regulatory/ Secretion | Phosphatidyl inositol transporter | 0 | 1 | 0 | 0 | 1 |

TABLE 3-continued

The induced genes encoding putative regulatory factors and selected for overexpression in *T. reesei*.

| | | | | | | | | |
|---|---|---|---|---|---|---|---|---|
| TRIRE0062244 | Regulation | Transcription factor | 0 | 0 | 0 | 0 | 1 |
| TRIRE0076677 | Regulation | Transcription factor | 0 | 0 | 0 | 0 | 1 |
| TRIRE0047317 | Regulation | Transcription factor | 0 | 0 | 0 | 0 | 1 |

| | Inducer | | | | | | |
|---|---|---|---|---|---|---|---|
| | Wheat | Spruce | Spruce | Spruce | Sophorose | Sophorose | Sophorose | Sophorose |
| | | | | | Time (h) | | | |
| Gene ID | 17 h | 0 h | 6 h | 17 h | 0 h | 6 h | 17 h | 41 h |
| TRIRE0108381 | 1 | 0 | 1 | 1 | 0 | 1 | 1 | 1 |
| TRIRE081972 | 1 | 0 | 1 | 1 | 0 | 0 | 1 | 0 |
| TRIRE0062244 | 1 | 0 | 0 | 1 | 0 | 0 | 1 | 1 |
| TRIRE0076677 | 1 | 0 | 1 | 1 | 0 | 0 | 0 | 1 |
| TRIRE0047317 | 1 | 0 | 1 | 1 | 0 | 1 | 1 | 0 |

Example 4

The primers used for amplification of the genes from *T. reesei* QM6a (CBS383.78) genome were as follows:

The 5' end primer contained a general part consisting of four 5' terminal G's, 25 nt attB1 site (ACAAGTTTGTACAAAAAAGCAGGCT) (SEQ ID NO:6) and a 8 nt region upsam from start codon of cbh1 gene (TGCGCATC), altogether forming the sequence GGGGACAAGTTTGTACAAAAAAGCAGGCTTGCGCATC (SEQID NO:7).

The general component of the oligo was followed by gene specific sequence corresponding to the 5' end of the gene.

The 3' end primer contained four 5' terminal G's, 25 nt attB2 site (ACCACTTTGTACAAGAAAGCTGGGT) (SEQ ID NO:8) and the nucleotides CTTA followed by the gene specific sequence corresponding to the 3' end of the gene.

The gene specific part of the primers were designed based on the ORF prediction in the genome version v2.0 or in some cases, as indicated below, according to the genome version v1.2.

The primers used for amplification of the genes using genomic *T. reesei* DNA as a template were the following:

pMH8 108381
(SEQ ID NO: 9)
5'GGGGACAAGTTTGTACAAAAAAGCAGGCTTGCGCATCATGGCGCTCTT

TGTCTGCTTGG pMH8 108381
(SEQ ID NO: 10)
3'GGGGACCACTTTGTACAAGAAAGCTGGGTCCTATTGTTGCTGCCCGCC

CCA pMH13 62244
(SEQ ID NO: 11)
5'GGGGACAAGTTTGTACAAAAAAGCAGGCTTGCGCATCATGCCACGCCC

AAAAGTCCACC pMH13 62244
(SEQ ID NO: 12)
3'GGGGACCACTTTGTACAAGAAAGCTGGGTATCAGAACCCAAACGCCCG

CGG pMH24 47317
(SEQ ID NO: 13)
5'GGGGACAAGTTTGTACAAAAAAGCAGGCTTGCGCATCATGTCGTCAAA

CGCTTCACCGG pMH24 47317
(SEQ ID NO: 14)
3'GGGGACCACTTTGTACAAGAAAGCTGGGTCCTAGCCCAAATGGCCCAT

ATTG pMH26 76677
(SEQ ID NO: 15)
5'GGGGACAAGTTTGTACAAAAAAGCAGGCTTGCGCATCATGGCCGACAC

CCCGACTC pMH26 76677
(SEQ ID NO: 16)
3'GGGGACCACTTTGTACAAGAAAGCTGGGTTTTAGAAGCCCGCCTGCTC

TGC pMH37 81972
(SEQ ID NO: 17)
5'GGGGACAAGTTTGTACAAAAAAGCAGGCTTGCGCATCATGACGGCCGA

GTACGAAG pMH37 81972
(SEQ ID NO: 18)
3'GGGGACCACTTTGTACAAGAAAGCTGGGTCTCGTTCATGCAGCAGCAG

PCR amplification reaction using the primers mentioned above resulted in DNA fragments containing the gene specific sequences described below inserted between the 5' and 3' terminal sequences originating from the general parts of the primers.

Example 5

Figure 8:
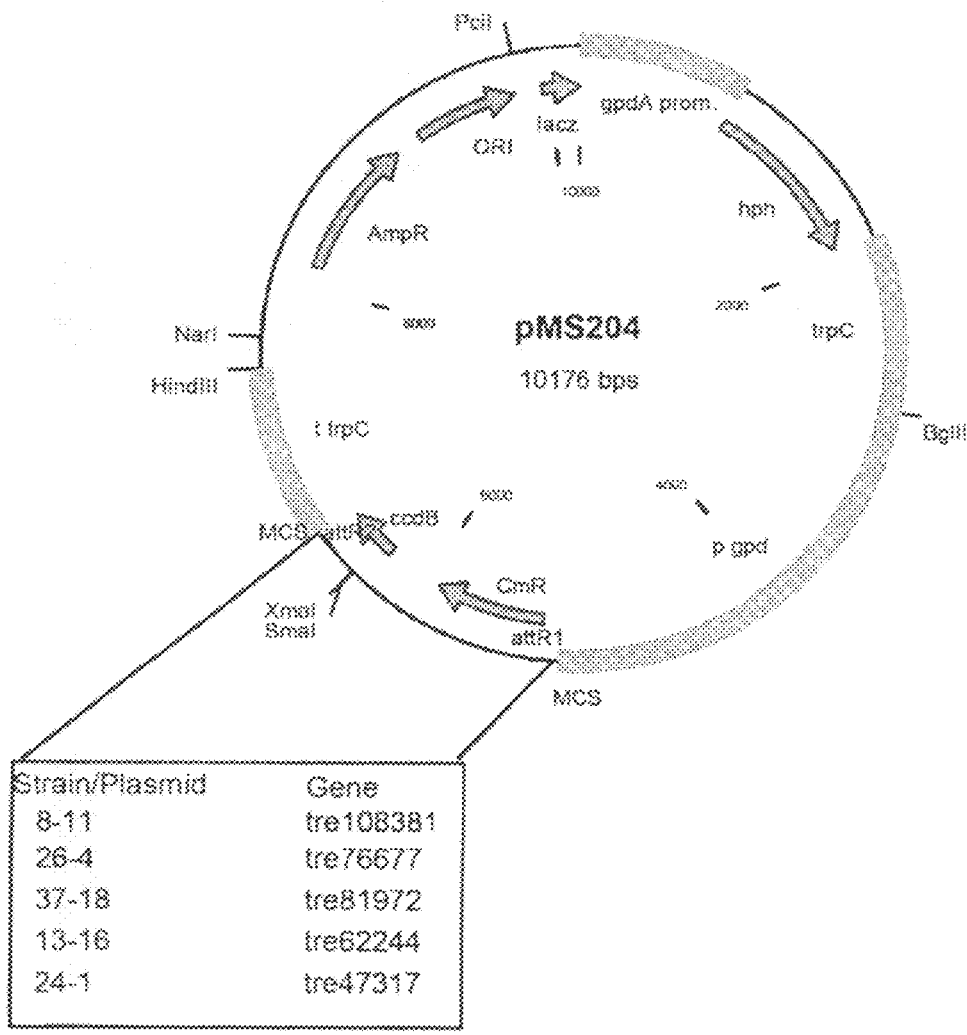
FIG. 8 Schematic view of the plasmid constructs made for transforming the strain *T. reesei* QM9414 and generating the strains overexpressing the genes encoding putative regulatory factors. The gene is inserted in the plasmid vector by replacing the region between attR1 attR2 sites containing the genes ccdB and CmR with the gene specific sequences. The names of the plasmids and the corresponding *T. reesei* strains obtained by transformation and the corresponding gene inserted in the plasmid are listed.

Construction of *T. reesei* Strains Overexpressing the Regulatory Genes Selected Based on the Transcriptome Data from the Induction Experiment on Avicel, Wheat, Spruce or Sophorose Containing Media The genes encoding putative regulatory factors co-expressed with known cellulase or hemicellulase genes were amplified by PCR from the *Trichoderma* genome (*T. reesei* QM6a; CBS383.78) and cloned into an expression vector which was then transformed into *T. reesei* QM9414. The transformants were selected based on function of the AmdS selection marker gene present in the expression cassette, transformants were purified from colonies originating from single spores, and the integration of the expression cassette into the genome was confirmed by PCR amplification of the cassette. Schematic view of the plasmids used for transformation is shown in FIG. 8.

Example 6

Cultivation of the *T. reesei* Strains Overexpressing the Putative Regulatory Factors, and Analysis of the Cultures for Growth and Protein Production The modified strains overexpressing genes encoding the putative regulatory factors were cultivated in shake flasks on medium containing 7.6 g/l $(NH_4)_2SO_4$, 15.0 g/l $KH_2PO_4$, 2.4 mM $MgSO_4.7H_2O$, 4.1 mM $CaCl_2.H_2O$, 3.7 mg/l $CoCl_2$, 5 mg/l $FeSO_4.7H_2O$, 1.4 mg/l $ZnSO_4.7H_2O$, 1.6 mg/l $MnSO_4.7H_2O$ and supplemented with 4% lactose and 2% spent grain extract. The cultures were analysed for growth and protein production, including assays for cellulase and hemicellulase activity. Cellulase activity was measured using 4-methylumbelliferyl-β-D-lactoside (MULac) as a substrate. The MULac can be used for measurement of combined activities of CBHI, EGI and BGL in *T. reesei* cultures (Bailey and Tahtiharju, 2003; Collen et al., 2005; van Tilbeurgh et al., 1982, 1985, 1988. Using a modified method MULac substrate can used also to measure the activities of CBHI and EGI specifically (Bailey and Tahtiharju, 2003; Collen et al., 2005; van Tilbeurgh et al., 1982, 1985, 1988). Xylanase activity was measured using birch xylan as a substrate (Bailey M. J., Biely P., and Poutanen, K., (1992) Interlaboratory testing of methods for assay of xylanase activity. J. Biotechnol. 23: 257-270). For the results on protein production in the cultures of the modified strains and the parental strain *T. reesei* QM9414, see the FIGS. 1-5.

Example 7

The closest homologue of a gene in another fungal species can be identified e.g. based on homology searches against genome databases using programs such as Blast. The homology searches can be done using either the nucleotide sequence of the gene or the amino acid sequence of the translated gene as a query. Information on the closest homologue of the gene can be obtained in any organism with a sequenced genome. Complete genome sequences are available for homology searches for a multitude of fungal species, and the number of fully sequenced fungal organisms is still increasing.

In this example, the translated sequences of the ORFs of the *T. reesei* genes tre81972, tre62244, 47317, 108381 and tre76677 were subjected to BLASTP homology search using protein sequence databases of a set of fungal species. The translated sequences of the *T. reesei* ORFs were according to JGI (Joint Genome Institute. The search was carried out using the fungal genome BLAST databases at NCBI containing completed genome sequence and whole genome shotgun sequence data with the corresponding protein sequences of a large number of fungal species. The databases used in the search in this example were:

Completed *Aspergillus fumigatus* proteins;
Completed *Aspergillus nidulans* FGSC A4 proteins;
Completed *Aspergillus terreus* proteins;
Completed *Chaetomium globosum* CBS 148.51 proteins;
Completed *Gibberella zeae* PH-1 proteins;

(The reference for the BLASTP 2.2.23+ program used: S. F. Altschul, T. L. Madden, A. A. Schaffer, J. Zhang, Z. Zhang, W. Miller, and D. J. Lipman (1997), "Gapped BLAST and PSI-BLAST: a new generation of protein database search programs", Nucleic Acids Res. 25:3389-3402. Reference for compositional score matrix adjustment: S. F. Altschul, J. C. Wootton, E. M. Gertz, R. Agarwala, A. Morgulis, A. A. Schaffer, and Y. K. Yu (2005) "Protein database searches using compositionally adjusted substitution matrices", FEBS J. 272:5101-5109.).

The parameters used in the searches were as follows:
General parameters:
Max target sequences: 100 (Maximum number of aligned sequences to display (the actual number of alignments may be greater than this)).
Short queries: Automatically adjust word size and other parameters to improve results for short queries.
Expect threshold: 10 (Expected number of chance matches in a random model)
Word size: 3 (The length of the seed that initiates an alignment)
Scoring Parameters:
Matrix: BLOSUM62 (Assigns a score for aligning pairs of residues, and determines overall alignment score)
Gap Costs: Existence:11, Extension:1 (Cost to create and extend a gap in an alignment)
Compositional adjustments: Conditional compositional score matrix adjustment (Matrix adjustment method to compensate for amino acid composition of sequences)
Filters and Masking:
Filter: Low complexity regions filter (Mask regions of low compositional complexity that may cause spurious or misleading results)

Table 4 shows examples of the closest homologues of the *T. reesei* genes in other fungal species obtained by the BLAST search, the closest homologue of tre81972 in *G. zeae*, tre62244 in *A. fumugatus*, tre47317 in *G. zeae*, tre108381 in *G. zeae* and tre76677 in *A. fumigatus*.

TABLE 4

Examples of the closest homologues of the *T. reesei* genes in selected fungal species based on the BLAST search

| | | | | | | | The best alignment | | |
|---|---|---|---|---|---|---|---|---|---|
| Query sequence | Query sequence length (amino acids) | Hit sequence | Species | Blast Score | Blast E-value | Identical amino acids per query length (%) | Identical amino acids/ length of the alignment | Identities in the alignment (%) | alignment length/ query length (%) |
| translated tre81972 | 450 | ref\|XP_385161.1\|FG04985.1 | *Gibberella zeae* | 526 | 4.00E−149 | 57 | 256/368 | 69 | 117 |

TABLE 4-continued

Examples of the closest homologues of the *T. reesei* genes in selected fungal species based on the BLAST search

| Query sequence | Query sequence length (amino acids) | Hit sequence | Species | Blast Score | Blast E-value | Identical amino acids per query length (%) | The best alignment Identical amino acids/ length of the alignment | Identities in the alignment (%) | alignment length/ query length (%) |
|---|---|---|---|---|---|---|---|---|---|
| translated tre62244 | 630 | ref\|XP_751028.1\| | *Aspergillus fumigatus* | 442 | 2.00E−123 | 45 | 285/654 | 43 | 70 |
| translated tre47317 | 596 | ref\|XP_389190.1\|FG09014.1 | *Gibberella zeae* | 587 | 3.00E−167 | 51 | 304/594 | 51 | 98 |
| translated tre108381 | 276 | ref\|XP_381845.1\|FG01669.1 | *Gibberella zeae* | 101 | 4.00E−21 | 24 | 66/166 | 39 | 37 |
| translated tre76677 | 675 | ref\|XP_748472.1\| | *Aspergillus fumigatus* | 697 | 0 | 52 | 354/680 | 52 | 103 |

The invention claimed is:

1. A method to genetically modify a *Trichoderma reesei* host for modified protein production, said method comprising:
    genetically modifying the host to be deficient of, with reduced or lacking amount or activity, or to overexpress, with increased amount or activity of gene tre108381 (SEQ ID NO:1) or coding region of SEQ ID NO:1, said host being capable of increased or decreased production of cellulase, hemicellulase or a protein that is expressed under a cellulase or a hemicellulase promoter.

2. The method according to claim 1, wherein the host is genetically modified to be deficient of gene tre108381 (SEQ ID NO:1) or coding region of SEQ ID NO:1, said host being capable of increased production of cellulase, hemicellulase, or a protein expressed under a cellulase or a hemicellulase promoter.

3. The method according to claim 1, wherein the host is genetically modified to overexpress gene tre108381 (SEQ ID NO:1) or coding region of SEQ ID NO:1, said host being capable of decreased production of cellulase, hemicellulase, or a protein expressed under a cellulase or a hemicellulase promoter.

4. A *Trichoderma reesei* host genetically modified to be deficient of or to overexpress gene [t]tre108381 (SEQ ID NO:1) or coding region of SEQ ID NO: 1, said host being capable of modified production of cellulases, hemicellulases, or a protein expressed under a cellulase or a hemicellulase promoter.

5. The host according to claim 4, wherein the host is genetically modified to be deficient of gene tre108381 (SEQ ID NO:1) or coding region of SEQ ID NO:1, said host being capable of increased production of cellulase, hemicellulase, or a protein expressed under a cellulase or a hemicellulase promoter.

6. The host according to claim 4, wherein the host is genetically modified to overexpress gene tre108381 (SEQ ID NO:1) or coding sequence of SEQ ID NO:1, said host being capable of decreased production of cellulase, hemicellulase, or a protein expressed under a cellulase or a hemicellulase promoter.

7. A method for improved production or for producing a modified composition of proteins in a *Trichoderma reesei* host, said method comprising a step of cultivating the modified filamentous fungus host of claim 4 under suitable culture conditions for protein production.

8. The method according to claim 7, wherein the protein is selected from the group consisting of cellulases, hemicellulases, and a protein expressed under a cellulase or a hemicellulase promoter.

9. The method according to claim 7, wherein the protein expressed under a cellulase or a hemicellulase promoter is a heterologous or recombinant protein.

* * * * *

UNITED STATES PATENT AND TRADEMARK OFFICE
CERTIFICATE OF CORRECTION

PATENT NO. : 9,499,826 B2
APPLICATION NO. : 13/701933
DATED : November 22, 2016
INVENTOR(S) : Tiina Pakula et al.

Page 1 of 1

It is certified that error appears in the above-identified patent and that said Letters Patent is hereby corrected as shown below:

On the Title Page

Item (73) first Column, the name of the Assignee reads:
TEKNOLOGIAN TUTKIMUSKESKUS VTT It should read:
TEKNOLOGIAN TUTKIMUSKESKUS VTT OY (VTT TECHNICAL RESEARCH CENTRE OF FINLAND LTD)

Signed and Sealed this
Eighteenth Day of April, 2017

Michelle K. Lee
*Director of the United States Patent and Trademark Office*

SEQUENCE LISTING

<160> NUMBER OF SEQ ID NOS: 18

<210> SEQ ID NO 1
<211> LENGTH: 1302
<212> TYPE: DNA
<213> ORGANISM: Trichoderma reesei

<400> SEQUENCE: 1

```
atggcgctct ttgtctgctt ggtgctgtcc cctggacgca tcactggagg ggggccggg       60
gggcacaacg acatcgtctg tggagaaggg ccgcggctgc ctggctggct gttcaacttg      120
tcaaatcctc cagcagcagc cgggtcgaga tataagaagc cgtgtttggc ctggattcat      180
aggttgctct gctgtctag tctatacgtt aaatcacctt gacagtcctc cttcagtctc      240
cctggccaac tgagcgttgc ttgtcgagat ccaagccatc actgcctctg ccaatgcgat      300
agtctgtcgg ctctcaagtg ccccaacacc cttcacatcg tttataccta tagcatctat      360
aggacaattg gaagcacttc ttctcatcgt ttcaccatct ccaatcagct cttactcctt      420
gcgctgctgt acctgaaact accttggtgc tatacaggac agacgcccaa cgtccatagc      480
catgtttaac acattcaaga tcgaccccga cgaacagc gtccaggagc tcaggcgggc       540
ctccgatccc atctcagccc ggtcgagcca gcaccaggcg tgcaacaact gccacgctaa      600
aaaggtataa agtcgcagca agcgcgccgc ttccagtcaa gtgatcaact ctgttgttgt      660
tcctgcgcta acagtcactc tcccccgatt agctcaagtg cagtggtgac aagagtggct      720
gtgagcgctg catcgccagc cagctgcgat gcgaatacac tcgctctccc tctcgcagag      780
gcggcaggaa gaccagcggc agaagctcca ctgacagccg tggcggattg gagccggccg      840
gtggtgacag cagccccggc agccagtctg gcaagtcgag gcacagaagc agcaggcact      900
tgcatgccgg gactagcagc agcagcagag cccgggcctc agcgtccagg gaggaagaat      960
atggcgatgc gttggacttg ttcgacccca cgacgctcgg tcctgacgat ggcttcgatc     1020
tacgatcctt atccttggag gcttcggaca gtggttacgg caacagtgcc tattacaacc     1080
agcagcagca gcagcagcag caacaacagc atggtgcagg aagctggcaa cacgtggcct     1140
ccagcgaccc gtacggcaac ttgtctggca gctcatacat gggcacgacc agctccagtg     1200
gccaagacta cgacgtggat tactacgaa actatgacga gtacggacag tatcatggcc     1260
agcaaaacga tcctagatac tggggcgggc agcaacaata gg                        1302
```

<210> SEQ ID NO 2
<211> LENGTH: 1469
<212> TYPE: DNA
<213> ORGANISM: Trichoderma reesei

<400> SEQUENCE: 2

| | | |
|---|---|---|
| atgacggccg agtacgaagg ttccgcgccg gccggccggg ttcagtcgtc gagctcggcc | 60 |
| agccagcagg cgggagtgtt cccaaacggc cacctgggcc acctgaacgc cgtccaggag | 120 |
| gaggccctgg ggcgcttcaa ggccgcgctg caggacaaga agctgtggcg cccggggccg | 180 |
| ccgccgtcgc acgacgacca gacgctgctg cggtatctgc gggcgaggcg ctggatcgtg | 240 |
| gacgatgcgc tggcccagtt caaggacacg gaggagtggg gggcggcgaa caacattgac | 300 |
| acgctgtacc ggacgattga gctggacgcg tacgagcaga gccggcgatt ggtgagtttc | 360 |
| attacgttgt tcttgttgtt gttgttgtag ttgttgtaca aggatctttg cttgtgtgat | 420 |
| atatatatat aaatcaaaaa actgacagca gaaaccttgc gacagtatcc ccaatggacc | 480 |
| ggccgccgag accgtcgagg catccctctc tacgtcttcg agatccgcac gctcgactcc | 540 |
| aaaaccatcg caaactacga gaagcagggc gccaacagca ccttttcaca ggccaagacg | 600 |
| gacggcaaga cgcctcccgg cctgctgcgg ctctttgccc tgtacgagaa cctgacgcgc | 660 |
| ttcaaccagc ccttttgcac acagctgacg gaccgcgaac accccgacgt gcccgtcacc | 720 |
| atgagcacca acattgttga catctcgggc gtcgggctca gcagttctg gaacctcaag | 780 |
| gggcacatgc aggcggcgtc gcagctggcc acggcgcatt accccgagac gctggaccgc | 840 |
| atcttcatca ttggcgcgcc cgtcttcttc agcaccgtct ggggctgggt gaagcgctgg | 900 |
| ttcgacccca tcaccgtctc caagatcttt gtgcttgcgc cgcacgaggt caagcccacg | 960 |
| ctcgaggcct ttatcgagcc ccggaacatc cccaagaagt acggcggcga gctcgactac | 1020 |
| accttttggcc agctgggcat cccagatcct gcatgggacg cgtcgtgcg gtgggagaag | 1080 |
| ggatacagct cgttccctag cgggccgctg ctgtgggagg acgtcccggg cgaggagaga | 1140 |
| ctggcgtgcg tgaggcttgg tgcggagaac ggcaagctgg tcagggaggt catctgcacg | 1200 |
| ctgcccagga catggagccc tcccgagagg actgtggacg agtcgaacca gacagacagc | 1260 |
| tcggccacca cctcgacgaa cacggccgcc acgacgatca acgacgcctc cgacgggact | 1320 |
| cagaccaccg aagatactct cgacgaggcc acgcagaccg aggggcctgc cgaagccatc | 1380 |
| gagaagctgg ctcttgacga cgacgacgac aaggccaaga cgccagaggt gacgccgata | 1440 |
| cctgccgcca ctgctgctgc atgaacgag | 1469 |

<210> SEQ ID NO 3
<211> LENGTH: 2441
<212> TYPE: DNA
<213> ORGANISM: Trichoderma reesei

<400> SEQUENCE: 3

| | | |
|---|---|---|
| atgccacgcc aaaagtccca cccgagccag cgccagcgcg ccgcagaggc atgcaatttc | 60 |
| tgccgcgcct ctaagaagcg atgcagtgcc accgttccct gcaccgcctg ccagaggcgc | 120 |
| ggcatcggtg actcgtgcca tctcacccac cggcctcgag gcttccgcgc ggcgccgctg | 180 |
| ccgctgccgc atccgccccg gacacgggct tcggctccgg ctccggagca ggtcccgggg | 240 |
| tcgccgagcg gtggagactg cgtcccggat gtccttcttg gcgatggtgc gtcgatgaac | 300 |
| gattcggcgt gggatcgaga gggggtttgga cagatggatg ctcccgagtg gtgctcggtg | 360 |
| aacggcggcg atgccgacgg gagctatcga ccgcttacac cgtcggattc tcgtgtgagc | 420 |

```
gtccctgagg ggactgccag ccgatctgca cgccagtcag cacgccagtc aagagcacgg      480
cgaagttctc ctgctccgga accagagtct catgctcgta tgcttctgaa tctacgagga      540
gaacgaggta cgtcgtgctg tgtctgatgg aatcggaatg tttgtccatg tgaagctgac      600
acgccagcct ttagtgtaca ttggcgaggc tgcgtctttg tcctttctcc agctgatacg      660
agataccgta acggcacaga tcggaccgtc acagttctct cataatgaga agcgcgatag      720
tatgctggag atggagcctt ctgcggcgga gtcgagcggc ttggggacgg ccagttgtaa      780
cattgacctg gagggcagtc tgctgtatac acggacattt gaagctgctg tgagtacgcc      840
cttgacatac cttggcttcc acataggagg aggatgatgc taacagtaca ttagactggc      900
ggcctattgg acgtctttgg gccaacagaa attgaagatc ttctcgtgaa aaccaaaact      960
gacgaggctc aatccctcaa cccgtgccag catgcctcca tcgacctcgt catagccatt     1020
ggcgctcagt gcaagtcccc cctcgaagcg cagcaggtcg ggccaccgta ttttcgacaa     1080
gcacagcagc gtgcctttgc cggcatgctg gaggatccaa acgtcgacat ggttcgcgca     1140
tttctcctca tggcctttta catgctcggc cactgccgga gaaatacggc gttcatgtac     1200
ttgggcatcg cggcgagagc tgcggttgct ctggggatgc acagccccca ttcttacacg     1260
gacttgaagg atcccgtgtg tcaacatagg taggctgaag tcggtcatct catggtcttc     1320
ttttttcaag gctgacgaag gcataggctt cacatttgga tgagtctctg tgttctggat     1380
atgcttgtga gctctatcct ggggaggccg cctgctacag ctggcctcag gcggagctt      1440 gacgccgcaa tcatcggttc caacagttcg tcagctacgc gccaaagtcc acgaaccgct     1500
ggcctctttg catcatacga aatactcacc atcataaacg aaagcatcga agcactctac     1560
ggcagaaaag tctcctcaac catcacggtg gagccgtact tgagcaaaat cgaagcctgg     1620
agcaaacgcc tgcccagctt tctccgcaac cctctcacga cgagaggaga tgcttctacc     1680
cagaaagctg caacggacag catacacgtt gcctgtctct actactttgc cattactctg     1740
gtcactcggc ccgtgctgat atcgagactc acttctcgcc cagatgtttc cacgccttcg     1800
tcctctcccc tggcgtctgc ctgtcttgat gcgggagtgt atctcataca ggcgtgttca     1860
gaggcgcata atctgggct actgctgggg aatatgtgca tcttgaagta agtcgttctt     1920
ctcctgctcc gtgcgaaacc tagtaacggg gaatagagct ctcatatttg ccgctggcct     1980
catactcgga ttcgacatgt ttgcgaaaaa ggagctcgac tacgaagtcg aagtagcctt     2040
tcgcagcgcc aaagacgttc tcgatttcct gggcgtccaa agcccccagg ctagtcatta     2100
ctctgaaatc ctcggcctat tgtctaatgc aatcatgaag cgacgcatgg aactgtcatc     2160
gcggcctcga agcaaatacg tcgggaagct attttccttt aatagagagg gccattcgga     2220
ccacgatgac agcgctggaa acgatgaagc gctgactttt gatgaccgta tcagtactac     2280
aggagtcacg gctagagagg ttgttggtga agtttggggt gcagatatgc cggcccaggc     2340
ggcggagatg gggggagacg tgttgcgagg ttggacgggt ttggagctgt ctcagtggga     2400
tagctttcct ttctttaatc cgcgggcgtt tgggttctga t                         2441
```

<210> SEQ ID NO 4
<211> LENGTH: 2301
<212> TYPE: DNA
<213> ORGANISM: Trichoderma reesei

<400> SEQUENCE: 4

```
atggccgaca ccccgactcg gtctgaggcc gacaacctca agagcttctc gtgtctgagc       60
```

```
tgtcgccagc gaaaggtcaa atgtgaccgc cgcgctccgt gcatcaactg cgtaaaggca    120
gagcgggcat gcagcttcgt cgcgccggtg cgtggcaaga ggaagcggac gaagccgcca    180
aaggagacgc tgcatgcgcg ggtgaagcgg tatgaggaga tgctcaaggc gtatggagcc    240
aagattgagc cttgtgagga tggagaagga tccgagtcgg agatggaaag cggcagcggg    300
aacggtaccc ctgagatggg gggcgacgtt gtgccgctga agttgcagac tggtcgtgcg    360
aatgaggaga agcccaagtt tatcatgaaa gagggagcat cgagatattt cgataggtat    420
gtcactctcc tctaattgta ccttcctacc tatggaacaa gaatggattc tcatacattg    480
actattatag tgccatctgg tccaacttat ctgatgaagt acatatcctg gcttctccat    540
cgccatcatt gcctccctac taacctatca cctagttcca acatccagag tcaaccaact    600
ttaacgatgt cggagaagcg attcccctttg agccagacgg caatctggac gagtcggggc    660
tcttctttga gccagagagc gaaaagattg aatcgcttgt caaactccat ctctcaacgc    720
cactgctgtc gaggctcaga gacatttaca aagaccgcgt cgacccgatg atgaagattc    780
tgcatctccc gacgttctgg gttaccatga caaacgcact gcagcgacct ctcgagatgc    840
ccaagggctt gcaatcgctc gtcttttgcgt ggtatctcgt cgcaatcagc tcgctcaagg    900
aagaagaggc acagaatctg ttcggagtgc cattgtcagc cattatgaaa cgctatcgag    960
ttgccacacg acaggccttg gtcaatgcca gattcctgtc gacttcaaac ctcatgactc   1020
ttcaagcctt ttccatctttt acggtaggta cagcacatca cagcccgttg ctcgtgcctg   1080
gtagatatgc tgacagacac cagatctgcg tcagaaatgt gtaccgctgc gacaccctct   1140
acatcctctc tggcgtcgcc atccgccttg cccgtaaaat gggcctccat cgcgacggca   1200
cattccttgg cctctcgccc tttgagacgg agatgcggcg tcgtctctgg tggcatctgg   1260
cgcacgtcga ctgtcggacg gcagacgtca tgggcacgaa gccctctccc gagatatcca   1320
gcggcgacgt gaagttgccc atcaacatcg acgatgacga gctatatccc gaaatgacct   1380
cgttcccaaa ggagcgcaac ggcatacacg cggtaactct gtgtctgctc aagtgcgagg   1440
ttatggagac gctgtgcaag tttgccaagg tctatcccac cgatctgcgc tgggagatgc   1500
tctacaatcc agagatctcc ctggcgggaa aggacagaat catcgaagcg gtggaggatc   1560
atctggaaag aaagtacttg cggtactgcg acccgtcgag ccccctggac accttcatct   1620
ccatcatggc gcgtcggca gtctgcaaaa tgaggctgtt cgcacacaat gtacgacagt    1680
ttgcacatct gtcggcaaaa gcctctcaag aggaccacga cgtctccttc ttcaacgcca   1740
tgaagctgct cgagtatgcc aacttgattc aaggaggaca catgggcctg acaagttca    1800 cgtggcagat aggcaccagc tatctctgga acacgatgct gtatcttctc atcgaggttc   1860
gcgcgcgcaa ggctcggccc gaggtcgaca aggcgtggaa gttgattggc gttgtctttg   1920
agcgctgccc tcaggtgttg gaggagttta acgggtccgt ctatgtcgcc ctgggcaaat   1980
ggaccctcga ggtctggaac tcttacgtcg ctgcatcaaa ggaagagggc cttccggagc   2040
cagtcgcacc gcagtatatt cacgatatcc gagaatggca gcggctcaag aaggagtcgg   2100
aagcgagggc gagacgcgac aaggcggagg caaggcccat gacgcggaat ccgtctgtcc   2160
atgacaagtt ttcgtatgcg gattatctgg aaggggggtt tcggacgtt cagtatttcc    2220 cgaacctgct gtcgtttgag acggatccga accagtggat gcagtgggag cagatggtgg   2280
cagagcaggc gggcttctaa a                                             2301
```

<210> SEQ ID NO 5
<211> LENGTH: 2583

<212> TYPE: DNA
<213> ORGANISM: Trichoderma reesei

<400> SEQUENCE: 5

| | | | | | |
|---|---|---|---|---|---|
| atgtcgtcaa | acgcttcacc | gggacctcac | aagcatccca | ggatactggc | ttgtgttttg | 60 |
| tgccagcatc | gcaaaatcaa | gtgcgaccgg | aattccccat | gttccaactg | tatcaaggtg | 120 |
| cgcgattcat | tttctccctt | gattgcttgg | tagcttgtag | ctaccgggtc | taatcacatg | 180 |
| tgctgtctgc | cgctcttctt | tcccagcctc | gaacttcgac | ctcaagcttg | tcatgggcat | 240 |
| cttgtatgcg | gaaatgggaa | ggaaaaagcg | actccagctc | gttgcctaat | ctttggatca | 300 |
| cacgaagctc | acattgccac | aggccaatgt | cacctgcact | cccagcaccc | cggcgccagc | 360 |
| tcgcaagcga | aggcgcccaa | accaagatct | ccaggaacgc | ctcgcgcgat | gcgaggagct | 420 |
| actcaagcag | tatgcaagtg | gaacggtgcc | gatacctgct | ccgtctactg | ctcaacggcc | 480 |
| gttaccacca | ttaccaacaa | cgccttcaaa | tcccaacttg | ccggcttccg | aggctcccgt | 540 |
| cgccacgccg | gccagcgtcg | attccacgca | gtctcgtaat | ccaggcgcgc | tcatggtgaa | 600 |
| ggaagatggc | aacgtccgat | tcatggatag | ctacatatgg | gctagtgtgt | acgacgaggt | 660 |
| gagtgaagtc | acgacacat | gcgctggccg | gtatgagcca | gggcctgggc | cgagggtttc | 720 |
| gagaccagcc | ccccgtcaac | attgctctac | aatgtgtgct | gactttaaag | agatgtacag | 780 |
| ctccagaaaa | tgcgggatat | tgttgagacg | gatgatccag | aagaaacgag | tctccttggg | 840 |
| tcggacgagc | tcactccaga | caacaatgca | gacctcgtgc | tttctgccga | cgtgttaac | 900 |
| accaacattg | acgatctgca | gcccgaccct | atccatattt | tccggctctg | gcagctctac | 960 |
| ctcgaccgcg | tcaaccccct | tttcaaagtc | attcacgtcc | gacgcttca | gccggtgata | 1020 |
| atggaagcag | cgacgaatat | gagcggcctg | cctatgcacc | aacaagctct | tcttttctcc | 1080 |
| atcttcgcca | tggcaagcct | ttcaatgact | tctgcagaga | gcatacaaac | cctcggcatg | 1140 |
| tctcgcgaag | ccgccatcca | gaaattcaac | actggtacca | aggcatgctt | gatcaaatac | 1200 |
| agcttcctca | agaattataa | catgacaacg | ttgcaatccc | tcgtcttata | cctggtaagt | 1260 |
| ctgatgagat | ctgacatctt | accttacctt | gatcttgccg | tctgagaact | gttgattgac | 1320 |
| aagatttcta | gctttctcta | gaaggacgat | atgcagacaca | tgcccaatgg | atcatcagcg | 1380 |
| gagtcattat | gcgtatagcc | cagaagatgg | gctatcaccg | cgatggtttg | caactaaacc | 1440 |
| tgacccctt | cgaaaccgaa | atgcgcaggc | gtatttggtg | gcagatcatg | atgctcgatg | 1500 |
| ccaaatgcgc | catgatgtct | ggcctcagcc | agtcgtggat | gaatcacgat | tgggacacca | 1560 |
| ggaggcccct | gaatctaaac | gatgcggacc | tattcccagg | ctctactgag | ccagtcgtgg | 1620 |
| agcgtgatgg | ccctacagaa | atggccttca | gcatcgtcat | tacggaagta | ttccgattca | 1680 |
| agatggaaac | agacggctcc | aacgagtccc | gtgccttcga | agctgccatc | atgggccaaa | 1740 |
| cgctcgacga | cagcgcggac | ccggaaaaca | caccaaggc | gatattcgag | aaattccgga | 1800 |
| aaaaggcaga | aaaactggaa | gagagactgc | tggagattga | aaagaacatg | atcgatgtga | 1860 |
| gggcaggcaa | cgcccacgtt | gcggcgcttg | ccatccggcc | aatgctcact | cataggttgt | 1920 |
| cggagatgct | tgtgcccatc | caagagcagc | cagaatgggg | gaccgagata | tttggtccca | 1980 |
| aagacaactt | cttcaaagtc | ctgctcatga | tgatggagca | taagatggag | gcgcacgagc | 2040 |
| aaatggtggc | agccggcttc | cagtggttca | tgaggtttca | ctttcagctt | gatgcctttg | 2100 |
| cagtcttcac | gggcctgctt | cacgatcgcc | cgatgggaac | actggcggac | cgcgcctggg | 2160 |
| aggttatgcg | caaggtttac | gccaaccatc | aagaattctc | tgacatgacc | atcaagccac | 2220 |

-continued

```
atgcggctca agctcaattt gtgctcaaag cctggcgagc gcgggagctg gcctacgccc    2280
agaatggcca agtgattgaa accccgagct tcatcaatcg tcttcgggaa ttggtgccct    2340
gcagcgattc caagtcgtct gggcagggtt ctgtgacttc tcccgcgacc acggtgacac    2400
ctcagcaaca gccactcatg ggtttcaacc agttcctcgg ggggtaccct gatgtttcca    2460
cagtgaattg ggacatgttt ggagaattga tgccaagtag cggagagcaa ctctccgccg    2520
ccatgtttga tggctacacc atgggcaacc tcgatatggg caatatgggc catttgggct    2580
agg                                                                  2583

<210> SEQ ID NO 6
<211> LENGTH: 25
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(25)
<223> OTHER INFORMATION: 5' end  primer: attB1 site

<400> SEQUENCE: 6
acaagtttgt acaaaaaagc aggct                                          25

<210> SEQ ID NO 7
<211> LENGTH: 37
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(37)
<223> OTHER INFORMATION: 5' end primer

<400> SEQUENCE: 7
ggggacaagt ttgtacaaaa aagcaggctt gcgcatc                             37

<210> SEQ ID NO 8
<211> LENGTH: 25
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(25)
<223> OTHER INFORMATION: 3' end primer: attB2 site

<400> SEQUENCE: 8
accactttgt acaagaaagc tgggt                                          25

<210> SEQ ID NO 9
<211> LENGTH: 59
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(59)
<223> OTHER INFORMATION: 5' end primer

<400> SEQUENCE: 9
ggggacaagt ttgtacaaaa aagcaggctt gcgcatcatg gcgctctttg tctgcttgg     59
```

```
<210> SEQ ID NO 10
<211> LENGTH: 51
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(51)
<223> OTHER INFORMATION: 3' end primer

<400> SEQUENCE: 10
ggggaccact ttgtacaaga aagctgggtc ctattgttgc tgcccgcccc a          51

<210> SEQ ID NO 11
<211> LENGTH: 59
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(59)
<223> OTHER INFORMATION: 5'end primer

<400> SEQUENCE: 11
ggggacaagt ttgtacaaaa aagcaggctt gcgcatcatg ccacgcccaa aagtccacc   59

<210> SEQ ID NO 12
<211> LENGTH: 51
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(51)
<223> OTHER INFORMATION: 3' end primer

<400> SEQUENCE: 12
ggggaccact ttgtacaaga aagctgggta tcagaaccca aacgcccgcg g          51

<210> SEQ ID NO 13
<211> LENGTH: 59
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(59)
<223> OTHER INFORMATION: 5' end primer

<400> SEQUENCE: 13
ggggacaagt ttgtacaaaa aagcaggctt gcgcatcatg tcgtcaaacg cttcaccgg   59

<210> SEQ ID NO 14
<211> LENGTH: 52
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(52)
<223> OTHER INFORMATION: 3' end primer

<400> SEQUENCE: 14
ggggaccact ttgtacaaga aagctgggtc ctagcccaaa tggcccatat tg         52
```

```
<210> SEQ ID NO 15
<211> LENGTH: 56
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(56)
<223> OTHER INFORMATION: 5' end primer

<400> SEQUENCE: 15
ggggacaagt ttgtacaaaa aagcaggctt gcgcatcatg ccgacacccc cgactc        56

<210> SEQ ID NO 16
<211> LENGTH: 51
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(51)
<223> OTHER INFORMATION: 3' end primer

<400> SEQUENCE: 16
ggggaccact ttgtacaaga aagctgggtt ttagaagccc gcctgctctg c             51

<210> SEQ ID NO 17
<211> LENGTH: 56
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(56)
<223> OTHER INFORMATION: 5' end primer

<400> SEQUENCE: 17
ggggacaagt ttgtacaaaa aagcaggctt gcgcatcatg acggccgagt acgaag        56

<210> SEQ ID NO 18
<211> LENGTH: 48
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(48)
<223> OTHER INFORMATION: 3' end primer

<400> SEQUENCE: 18
ggggaccact ttgtacaaga aagctgggtc tcgttcatgc agcagcag                 48
```